United States Patent [19]
Greene et al.

[11] Patent Number: 5,846,984
[45] Date of Patent: Dec. 8, 1998

[54] USE OF CICLOPIROX OR A PHARMACEUTICALLY ACCEPTABLE SALT THEREOF FOR INHIBITING NEURONAL CELL DAMAGE OR NEURONAL CELL DEATH

[75] Inventors: Lloyd A. Greene, Larchmont; Stephen E. Farinelli, New York, both of N.Y.

[73] Assignee: The Trustees of Columbia University in the City of New York, New York, N.Y.

[21] Appl. No.: 588,764

[22] Filed: Jan. 19, 1996

[51] Int. Cl.$^6$ ..................................................... A61K 31/44
[52] U.S. Cl. ................................................................ 514/350
[58] Field of Search ............................................... 514/350

[56] References Cited

U.S. PATENT DOCUMENTS

| | | | |
|---|---|---|---|
| 3,644,626 | 2/1972 | Witzel | 424/263 |
| 3,655,897 | 4/1972 | Witzel | 424/263 |
| 3,883,545 | 5/1975 | Lohaus et al. | 260/297 Z |
| 4,185,106 | 1/1980 | Dittmar et al. | 424/263 |
| 4,711,775 | 12/1987 | Dittmar et al. | 424/70 |
| 5,231,112 | 7/1993 | Janoff et al. | 514/401 |

FOREIGN PATENT DOCUMENTS

| | | | |
|---|---|---|---|
| 9205190 | 4/1992 | WIPO . | |

OTHER PUBLICATIONS

*Abstracts*, 19: 885 (1993).

Ferrari, G. and Greene, L.A. (1994). Proliferative inhibition by dominant–negative Ras rescues naive and neuronally differentiated PC12 cells from apoptotic death. *The EMBO Journal*, 13: 5922–5928 and;.

Brooks, S.F. et al., (1993). Apoptosis induced by NGF–withdrawal from differentiated PC12 cells involved activation of $p34^{cdc2}$ kinase. *Society For Neuroscience Abstracs*, 19: 885.

Farinelli, S.E. et al., (1993). A possible link between the cell cycle and apoptosis of PC12 cells. *Society For Neuroscience*.

Urbani, L. et al., (1995). Dissociation of nuclear and cytoplasmic cell cycle progression by drugs employed in cell synchronization. *Experimental Cell Research*, 219: 159–168.

*Primary Examiner*—Theodore J. Criares
*Attorney, Agent, or Firm*—John P. White; Cooper & Dunham LLP

[57] ABSTRACT

6-Cyclohexyl-1-hydroxy-4-methyl-2(1H)-pyridinone, also known as ciclopirox, and its salts such as ciclopirox olamine are used to inhibit neuronal cell damage or neuronal cell death.

12 Claims, 28 Drawing Sheets

USE OF CICLOPIROX OR A PHARMACEUTICALLY ACCEPTABLE SALT THEREOF FOR INHIBITING NEURONAL CELL DAMAGE OR NEURONAL CELL DEATH

The invention disclosed herein was made with Government support under NIH Grant No. NS 33689-01 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The mechanisms by which nerve growth factor (NGF) and other neurotrophic agents promote neuronal survival is currently unresolved. Cultured sympathetic neurons deprived of NGF undergo apoptotic death (Edwards et al., 1991; Batistatou and Greene, 1993; Deckwerth and Johnson, 1993; Edwards and Tolkovsky, 1994) and have been valuable for investigating mechanisms of survival and death Deckwerth and Johnson, 1993; Edwards and Tolkovsky, 1994; Greenlund et al., 1995).

The PC12 rat pheochromocytoma cell line (Greene and Tischler, 1976) also has been used as a model to study the mechanism of apoptotic neuronal death following withdrawal of trophic support. In serum-containing medium PC12 cells divide and display many characteristics of adrenal chromaffin cells. Within several days of NGF exposure, these cells stop dividing and acquire numerous properties of mature sympathetic neurons (reviewed by Greene and Tischler, 1982; Guroff, 1985). When cultured in serum-free medium without NGF, both naive and neuronally-differentiated (NGF-pretreated) PC12 cells die by an apoptotic mechanism (Greene, 1978; Batistatou and Greene, 1991). Addition of NGF to the cells in serum-free medium rescues them from death. Because both naive, proliferating and neuronally-differentiated, non-proliferating PC12 cells are sustained by NGF under serum-free conditions, the line may be used to model the survival mechanisms of both neuroblasts and postmitotic neurons.

Studies with neuronally-differentiated PC12 cells reveal that, as with sympathetic neurons (Martin et al., 1988), death caused by withdrawal of trophic support is retarded by RNA and protein synthesis inhibitors (Mesner et al., 1992; Pittman et al., 1993). In contrast, such inhibitors do not prevent death of naive PC12 cells (Rukenstein et al., 1991). It was suggested that this difference in behavior illuminates the underlying role of NGF and other trophic agents in promoting cell survival. For dividing neuroblast-like naive PC12 cells, it was hypothesized that trophic factors such as NGF are required for successful cell cycle traverse and that in the absence of such support, an abortive and fatal cycle occurs (Batistatou and Greene, 1993; Ferrari and Greene, 1994). This proposal is supported by a number of recent findings with non-neuronal cells (Evan et al., 1992; Yonish-Rouach et al., 1991;1993; Colombel., 1992; Shi et al., 1994). In the case of neuroblasts, cell cycle molecules are constitutively expressed and, hence, attempted replication and death are independent of synthesis. In contrast, for non-dividing neurons and NGF-pretreated PC12 cells, it was proposed that RNA and protein synthesis blockers prevent neuronal death because they suppress production of proteins required for attempted cycle re-entry (Ferrari and Greene, 1994). In consonance with this, long-term NGF exposure exerts anti-mitogenic actions on PC12 (Greene and Tischler, 1976; Ferrari and Greene, 1994) and chromaffin cells (Tischler et al., 1993). Also, Freeman et al., (1994) reported that the G1 cyclin, D1, is induced during death of NGF-deprived sympathetic neurons while Brooks et al., (1993 Soc. Neurosci. Abstr. 19:885) observed that withdrawal of NGF from neuronally differentiated PC12 cells triggers re-appearance of M-phase-associated cdc2 activity.

It was reported-that suppression of proliferative capacity in both naive and neuronally-differentiated PC12 cells by over-expression of dominant-negative ras or by treatment with N-acetylcysteine protects them from removal of trophic support (Ferrari and Greene, 1994).

SUMMARY OF THE INVENTION

The present invention provides a method of inhibiting neuronal cell damage or neuronal cell death in a subject comprising administering to the subject 6-cyclohexyl-1-hydroxy-4-methyl-2(1H)-pyridinone or a pharmaceutically acceptable salt thereof, the 6-cyclohexyl-1-hydroxy-4-methyl-2(1H)-pyridinone or salt thereof being present in an amount effective to inhibit neuronal cell damage or neuronal cell death in the subject.

The present invention also provides a pharmaceutical composition comprising 6-cyclohexyl-1-hydroxy-4-methyl-2(1H)-pyridinone or a pharmaceutically acceptable salt thereof in an amount effective to inhibit neuronal cell damage or neuronal cell death, and a pharmaceutically acceptable carrier.

DETAILED DESCRIPTION OF THE INVENTION

Figure 11:
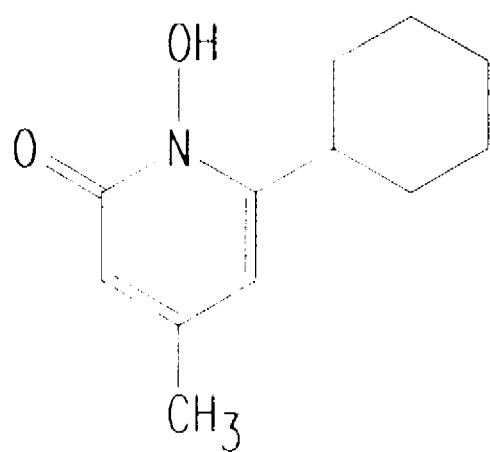
FIG. 11 shows the chemical structure of 6-cyclohexyl-1-hydroxy-4-methyl-2(1H)-pyridinone, also known as ciclopirox.

The present invention provides a method of inhibiting neuronal cell damage or neuronal cell death in a subject comprising administering to the subject 6-cyclohexyl-1-hydroxy-4-methyl-2(1H)-pyridinone or a pharmaceutically acceptable salt thereof, the 6-cyclohexyl-1-hydroxy-4-methyl-2(1H)-pyridinone or salt thereof being present in an amount effective to inhibit neuronal cell damage or neuronal cell death in the subject. The 6-cyclohexyl-1-hydroxy-4-methyl-2(1H)-pyridinone is also known as ciclopirox (see FIG. 11).

In one embodiment of the invention, the subject is a mammal such as a human or a mouse.

In another embodiment of the invention, the neuronal cell damage or neuronal cell death is associated with a traumatic injury.

The term "traumatic injury" is used herein to designate a physical injury that severs or damages nerve fibers.

In yet another embodiment of the invention, the neuronal cell damage or neuronal cell death is associated with a stroke.

In another embodiment of the invention, the neuronal cell damage or neuronal cell death is associated with a disease selected from the group consisting of Parkinson's disease, amyotrophic lateral sclerosis, and Alzheimer's disease.

In yet another embodiment of the invention, the effective amount of 6-cyclohexyl-1-hydroxy-4-methyl-2(1H)-pyridinone or salt thereof is from about 5 mg/Kg of body weight to about 30 mg/Kg of body weight per day.

In another embodiment of the invention, wherein the effective amount of 6-cyclohexyl-1-hydroxy-4-methyl-2(1H)-pyridinone or salt thereof is from about 10 mg/Kg of body weight to about 20 mg/Kg of body weight per day.

In yet another embodiment of the invention, the salt is the ethanolamine salt of 6-cyclohexyl-1-hydroxy-4-methyl-2(1H)-pyridinone, also known as ciclopirox olamine.

In another embodiment of the invention, the 6-cyclohexyl-1-hydroxy-4-methyl-2(1H)-pyridinone or salt thereof is administered orally, intravenously, subcutaneously, intramuscularly, topically, parenterally, by inhalation, rectally, or intraocularly.

The present invention further provides a method of treating neuronal cell damage or neuronal cell death in a subject comprising inhibiting neuronal cell damage or neuronal cell death.

The present invention also provides a pharmaceutical composition comprising 6-cyclohexyl-1-hydroxy-4-methyl-2(1H)-pyridinone or a pharmaceutically acceptable salt thereof in an amount effective to inhibit neuronal cell damage or neuronal cell death, and a pharmaceutically acceptable carrier.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In one embodiment of the invention, the neuronal cell damage or neuronal cell death is associated with a traumatic injury.

In another embodiment of the invention, the neuronal cell damage or neuronal cell death is associated with a stroke.

In another embodiment of the invention, the neuronal cell damage or neuronal cell death is associated with a disease selected from the group consisting of Parkinson's disease, amyotrophic lateral sclerosis, and Alzheimer's disease.

In another embodiment of the invention, the effective amount of 6-cyclohexyl-1-hydroxy-4-methyl-2(1H)-pyridinone or salt thereof is from about 200 mg to about 4500 mg per daily dosage.

In yet another embodiment of the invention, the effective amount of 6-cyclohexyl-1-hydroxy-4-methyl-2(1H)-pyridinone or salt thereof is from about 400 mg to about 3000 mg per daily dosage.

In another embodiment of the invention, the salt is the ethanolamine salt of 6-cyclohexyl-1-hydroxy-4-methyl-2(1H)-pyridinone, also known as ciclopirox olamine.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

This study investigates whether apoptotic neuronal cell death caused by withdrawal of trophic support can be prevented by agents that block cell cycle progression. Three G1/S blockers are shown to be effective in this regard whereas agents that block at later stages in the cycle, are not.

Experimental Procedures

PC12 Cell Culture

PC12 cell cultures (passage 26–34) were maintained as previously described (Greene and Tischler, 1976; Greene et al., 1991) in RPMI 1640 medium supplemented with 10% horse serum and 5-fetal bovine serum (15% serum, complete medium) and seeded on collagen-coated plastic cell culture dishes (Falcon). For the studies involving neuronally differentiated PC12 cells, naive cells were washed free of serum by three cycles of centrifugation/resuspension in RPMI 1640 medium. The cells were then replated onto 150 mm collagen-coated plastic dishes in the presence of 100 ng/ml NGF and harvested for survival studies 10–14 days later.

Assay for PC12 cell survival in serum-free or NGF-free conditions.

Cell survival was assayed as previously described (Rukenstein et al., 1991; Batistatou and Greene, 1991). Briefly, cells were washed extensively with serum-free RPMI 1640 medium (five times on the dish followed by five cycles of centrifugation/resuspension) and replated into collagen-coated 24-well tissue culture dishes at a density of $2 \times 10^5$ per well in a volume of one ml in the presence of various cell cycle blockers. Unless otherwise noted, cells were pretreated overnight (approx. 16 hours) with the cell cycle blockers prior to serum deprivation. The drugs were not included in the cell washing steps. At daily intervals, cells were lysed and intact nuclei were counted using a hemacytometer (Soto and Sonnenschein, 1985). In this assay, nuclei of dead cells generally disintegrate or, if in the process of apoptosis, appear pyknotic and irregularly shaped. In contrast, nuclei of living cells are phase bright and have clearly defined limiting membranes. Cell counts were performed on triplicate wells. The data are expressed as a percentage of the cell number initially plated.

$[^3H]$-Thymidine Incorporation

PC12 cells were plated in collagen-coated 24-well plates at a density of $4 \times 10^5$/well in RPMI 1640 serum-free medium containing 3 $\mu$M insulin (Sigma) or NGF (100 ng/ml). It was necessary to add these growth factors to the serum-free cultures to prevent the control cultures from dying. Immediately upon plating, cultures were treated with the indicated cell cycle blocker at various concentrations and for various lengths of time prior to exposure to a 1 hour pulse of $[^3H]$-thymidine (1 $\mu$Ci per ml). The cultures were washed 3 times with 1 ml ice-cold PBS and then extracted with 1 ml ice-cold 10% TCA at 4° C. for 1 hour. The TCA-insoluble material was solubilized overnight with 0.3 ml 1M NaOH, transferred to a scintillation vial, neutralized with HCl and then quantified by liquid scintillation counting. Background counts were taken as those from cultures which had been treated with 10 $\mu$M aphidicolin, which in this paradigm routinely inhibited thymidine incorporation by more than 98%. Data are presented as the percentage of TCA insoluble counts relative to those on replicate untreated control cultures. All measurements were performed in triplicate.

Nuclear staining of PC12 cells with Hoechst 33342

PC12 cells (both control and drug-treated) were deprived of serum as described above and plated on poly-D-lysine coated chamber slides. Twenty-four hours after plating, cells were fixed with 4% paraformaldehyde in phosphate buffered saline (PBS) for 1 hour then exposed to 1 $\mu$g/ml Hoechst 33342 (Sigma) in PBS for 30 minutes, then rinsed once more with PBS. Cells were examined under UV illumination using a Zeiss Axiovert microscope. Nuclei were scored as normal or pyknotic.

Alamar Blue assay for viability in serum-free medium

Serum-deprived PC12 cells were plated for assay of survival as described above. At the time of plating, 0.1 ml Alamar Blue solution (Alamar Biosciences, Inc.) was added to each well and cultures were placed in a 37° C. $CO_2$ (7.5%) incubator for 4 hours. After this time, a 0.5 ml aliquot of medium was removed from each culture, diluted with 0.5 ml $H_2O$ and the difference in its absorbance at 570 and 600 nm was determined. Blanks consisted of culture medium containing the indicated cell cycle blocker and Alamar Blue, but no cells. At subsequent time points, this procedure was repeated on replicate plates. In this assay, living (but not dead) cells take up, metabolize and release the dye, causing a change in its absorbance. Data are expressed as the percentage change in absorbance relative to that obtained from cultures initially following plating. The length of incubation with Alamar Blue and the number of cells per well were chosen because we had determined that the viability measurement was linear in this range. All measurements were performed in triplicate.

Culture and survival assay of sympathetic neurons

Primary cultures of sympathetic neurons were prepared from the dissociated superior cervical ganglia of postnatal day 2 rats (Lee et al., 1980). Cells were plated at a density of 0.5 ganglion per well in 24-well collagen-coated plastic dishes. Cultures were grown in RPMI 1640 medium containing 10% heat-inactivated horse serum and 100 ng/ml mouse NGF. One day following plating, uridine and 5-fluorodeoxyuridine (10 $\mu$M each) were added to the cultures and left for three days to eliminate non-neuronal cells. On the sixth day following plating, NGF was removed by washing the cultures three times with RPMI 1640 medium containing 10% horse serum, followed by the addition of 0.5 ml of the same medium containing antibody against mouse NGF (1:200 dilution, Sigma) and the indicated cell cycle blocker. Toxicity of the pharmacological agents was assessed by adding back 100 ng/ml NGF in replicate cultures following the initial NGF washout. Viability of the neurons was assessed by counting the number of intact, phase bright neurons in each well by the method of strip counting (Greene et al., 1978; Rydel and Greene, 1988). Dead neurons lost their phase bright appearance and disintegrated leaving behind cellular debris. This determination was made on the initial day of NGF withdrawal and then on subsequent days. Results are expressed as the percentage of viable neurons relative to that present initially following NGF withdrawal. In the studies evaluating the effectiveness of ciclopirox (CPX), neurons were cultured for only three days in the presence of NGF prior to its removal and addition of CPX because it was found that the cells died more rapidly in this paradigm.

The response of the cells treated with the G1/S blockers was examined when the compounds were withdrawn and NGF was added back. Neurons were grown in the presence of NGF for three days, the NGF was removed as described above and treated with the indicated agents. After 36 hours, the cultures were washed once with 1 ml of RPMI containing 10% horse serum, and then refed with 0.5 ml of the same medium containing 100 ng/ml human recombinant NGF, to which the anti-mouse NGF does not cross react. The neurons were examined for viability as described above.

Assay of protein synthesis

Naive PC12 cells and primary sympathetic neurons were prepared and plated in 24-well collagen-coated dishes as described above. Cultures were pretreated with various concentrations of mimosine for 4 hours prior to the addition of 5 $\mu$Ci [$^3$H]-leucine per well. Following a 16 hour incubation, the cultures were washed, TCA-extracted, solubilized and subjected to liquid scintillation counting as described above for the measurement of [$^3$H]-thymidine incorporation. The level of background [$^3$H]-leucine incorporation was determined by pretreating replicate cultures with 1 $\mu$g/ml cycloheximide, and subtracting the resulting value from all of the samples. In all studies this concentration of cycloheximide caused a >95% inhibition of [$^3$H]-leucine incorporation.

Results

CPT-cAMP blocks both PC12 cell cycle progression and death

Figure 1:
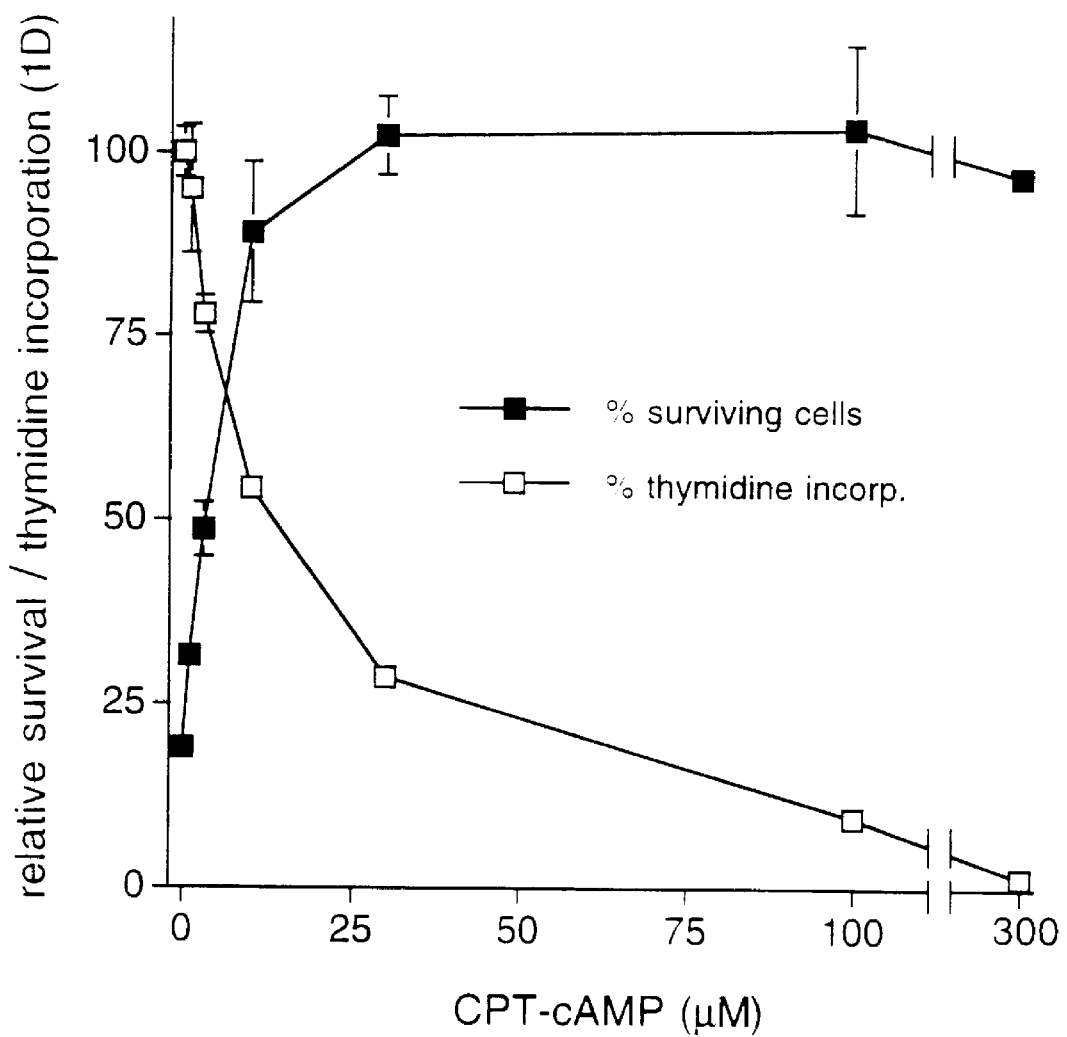
FIG. 1 shows dose-response relationships for promotion of survival of PC12 cells in serum-free medium (1 day) and inhibition of [$^3$H]-thymidine incorporation by CPT-cAMP. Cell survival data are expressed relative to the number of cells initially plated while thymidine incorporation data are expressed relative to untreated control cultures. For survival studies, cells were not pretreated with CPT-cAMP prior to serum deprivation. Assay of [$^3$H]-thymidine incorporation was conducted following a 24 hour pretreatment with CPT-cAMP. Data are the mean±SEM of three samples. In this and subsequent figures, the absence of error bars indicates that the error was smaller than the symbol used.

Past findings demonstrated that the cyclic AMP analog chlorphenylthio-cAMP (CPT-cAMP) prevents the death of trophic factor-deprived PC12 cells and neurons (Rydel and Greene, 1988; Rukenstein et al., 1991). To examine whether this effect might be related to the cell cycle, we tested the ability of CPT-cAMP to prevent DNA replication in serum-containing medium in parallel with its ability to prevent the death of serum-deprived PC12 cells. In the typical assay for serum-free survival, 65–75% of PC12 cells die after one day and virtually all die by 4 days. As shown in FIG. 1, there is a very close correlation of the dose-response relationships between the ability of CPT-cAMP to inhibit thymidine incorporation and to promote survival of PC12 cells in serum-free medium. CPT-cAMP acts very rapidly to block DNA synthesis, for within 2 hour of treatment with 100 $\mu$M CPT-cAMP, [$^3$H]-thymidine incorporation is blocked by 75%; inhibition is complete by 24 hours. As demonstrated previously, it is not necessary to pretreat PC12 cells with CPT-cAMP prior to serum deprivation to obtain complete survival (Rukenstein et al., 1991).

The finding that CPT-cAMP causes cessation of PC12 cell proliferation and promotes survival prompted us to further examine the prediction that blocking cell cycle progression may prevent cell death following trophic factor withdrawal. We therefore tested a battery of agents which have been shown to block cell cycle transit at specific points for their ability to prevent the death of trophic factor-deprived PC12 cells and sympathetic neurons. All agents were first tested for their ability to block the incorporation of [$^3$H]-thymidine into DNA so that experiments would employ appropriate concentrations and lengths of pretreatment.

Figure 2A:
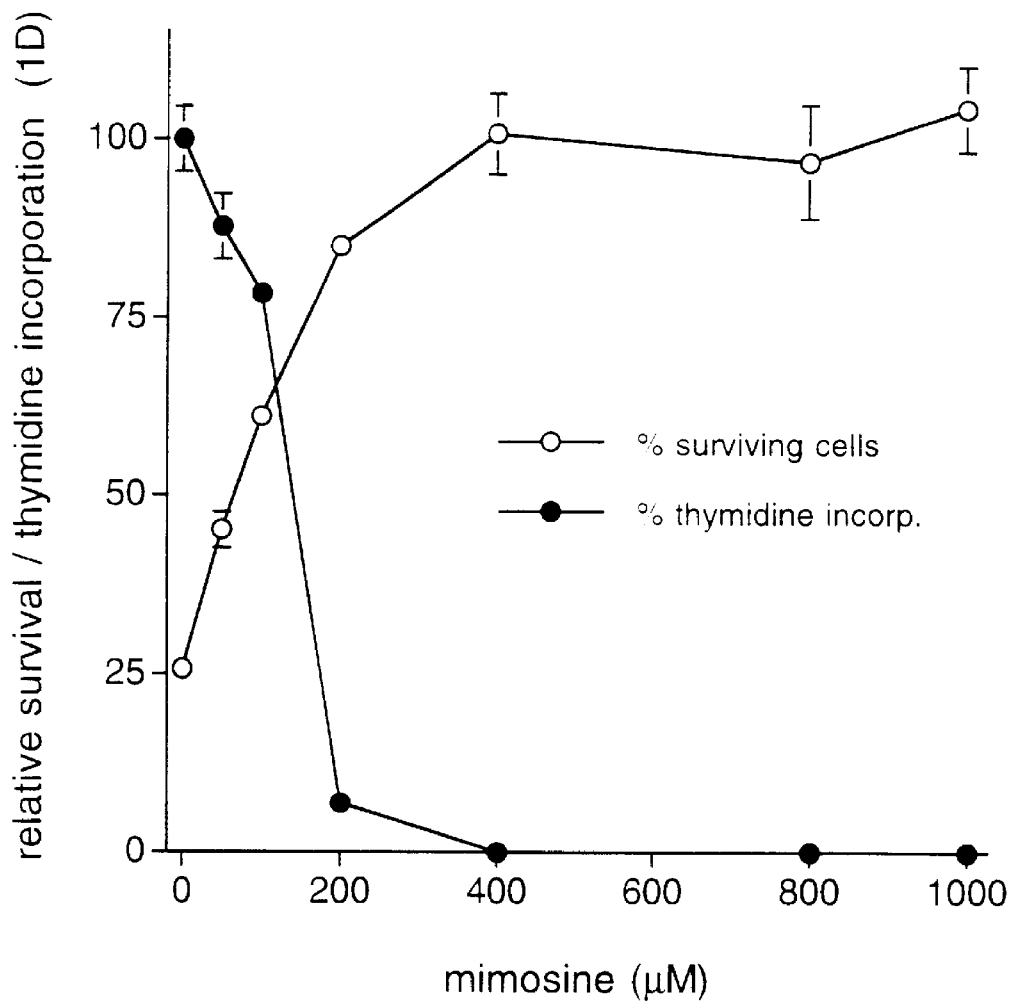
FIGS. 2A and 2B and 2C show that mimosine promotes survival of PC12 cells in serum-free medium and inhibits [$^3$H]-thymidine incorporation. Dose-response relationships for promotion of survival at 1 day and inhibition of thymidine incorporation by mimosine (A). For survival studies, cells were pretreated with mimosine for 16 hours prior to serum deprivation. Assay of [$^3$H]-thymidine incorporation was conducted following a 24 hour pretreatment with mimosine. Pretreatment with mimosine enhances its protective effect on serum-deprived PC12 cells (B). Pretreated cells were exposed to 400 µM mimosine for 16 hours prior to serum-deprivation. $^a$Significantly greater than untreated control (p<0.05). $^b$Significantly less than mimosine-pretreated cultures (p<0.05). Time course of survival in serum-free conditions (C). All data are the mean±SEM of 3 samples.
Figure 2B:
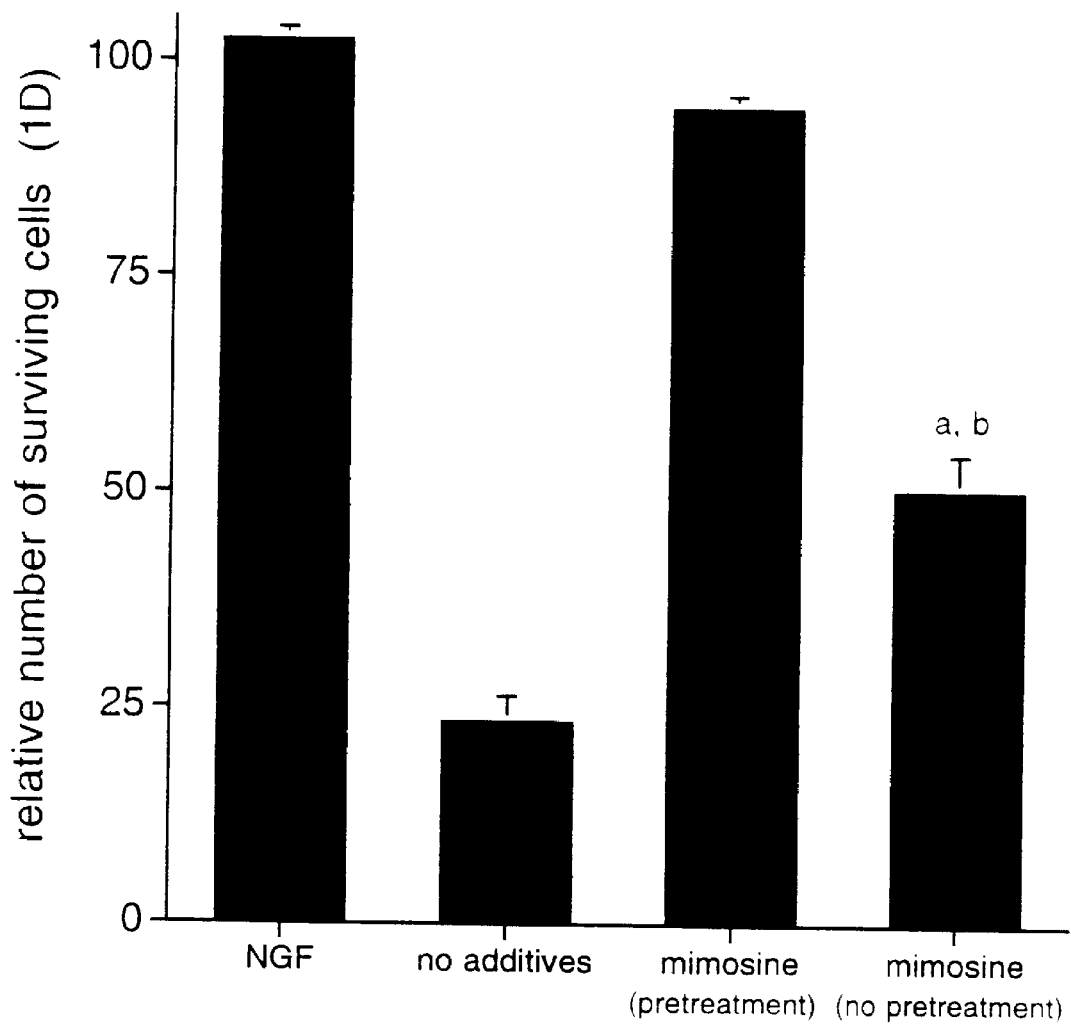
Figure 2C:
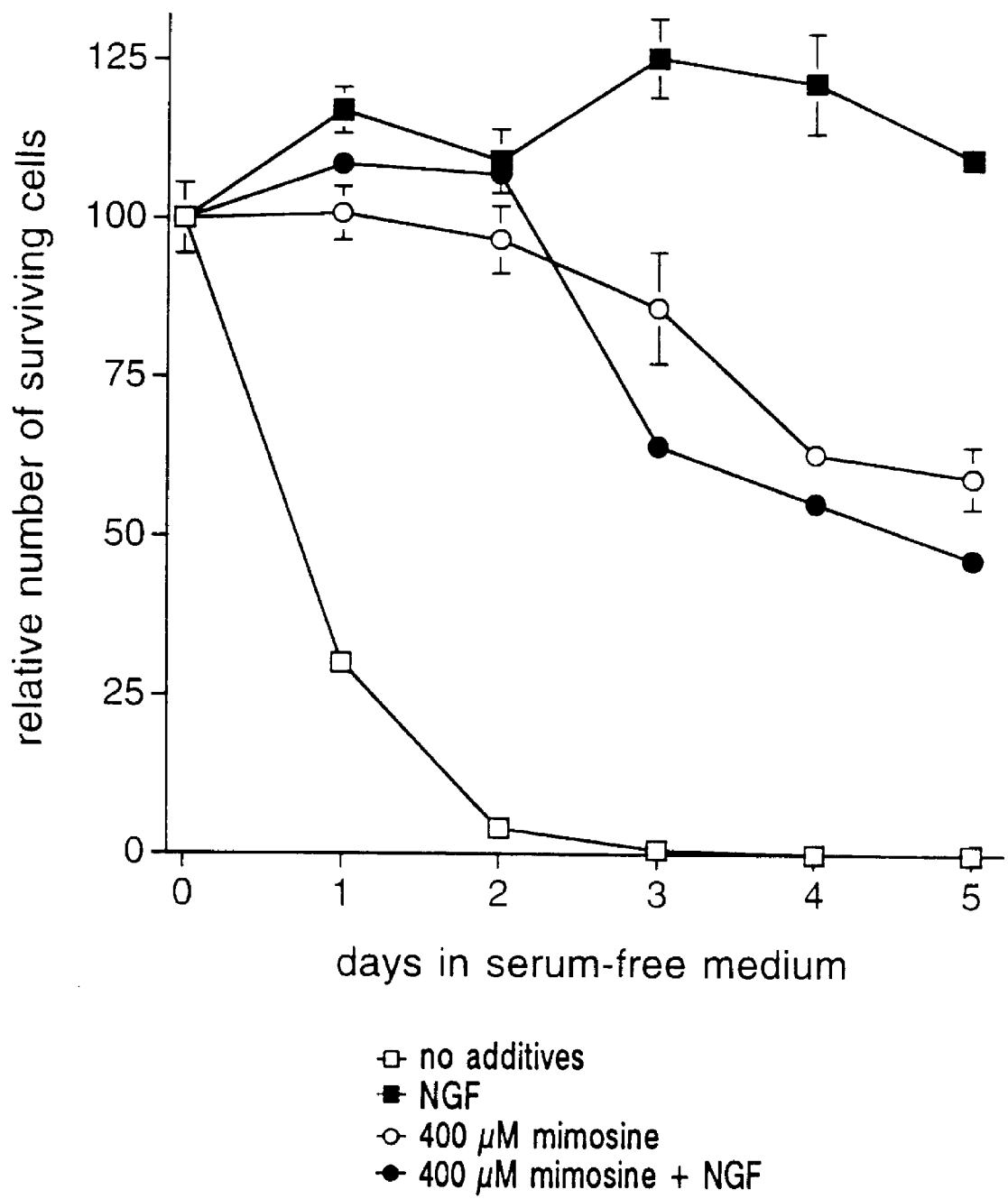

The G1/S blockers mimosine, ciclopirox and deferoxamine prevent the death of serum-deprived PC12 cells Mimosine is an agent that blocks cells prior to the G1/S transition point by a mechanism that is still unclear (Lalande, 1990). This drug blocks thymidine incorporation completely in dividing PC12 cells at concentrations of 300–400 $\mu$M within four hours (FIG. 2A). As shown in FIGS. 2A and FIGS. 3A, 3B, 3C, and 3D, mimosine prevented the death of serum-deprived PC12 cells in a concentration-dependent fashion and was maximally effective at 400 $\mu$M. Comparison of the curves FIGS. 2A reveals a close correlation between the concentration of mimosine required to inhibit DNA synthesis and to prevent the death of serum-deprived PC12 cells. Unlike rescue by CPT-cAMP and other survival factors, it was necessary to pretreat cells with mimosine overnight prior to serum deprivation in order to obtain complete survival (FIG. 2B). FIG. 2C illustrates the long-term effects of mimosine treatment on survival in this paradigm. Survival up to three days was excellent (>856%). However mimosine was unable to promote full survival beyond this time. This appeared due to toxicity, because even when NGF was present in combination with mimosine there was a comparable loss of cell viability.

Figure 3A:
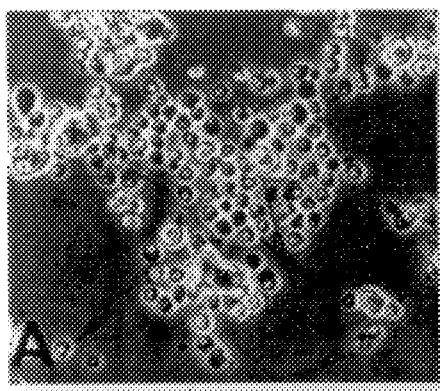
FIGS. 3A, 3E, 3C, and 3D show phase contrast micrographs of PC12 cells maintained in serum-free conditions for 24 hours with no additives (A); 100 ng/ml NGF (2); 400 µM mimosine (C); 1 mM deferoxamine (D). Magnification is 375×.
Figure 3B:
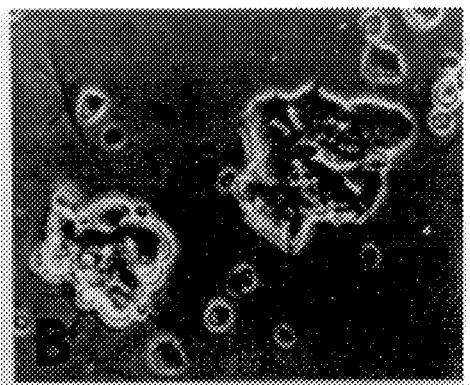
Figure 3C:
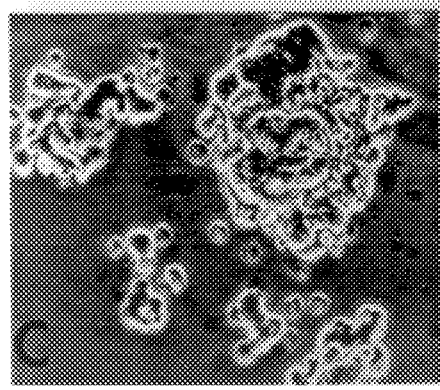
Figure 3D:
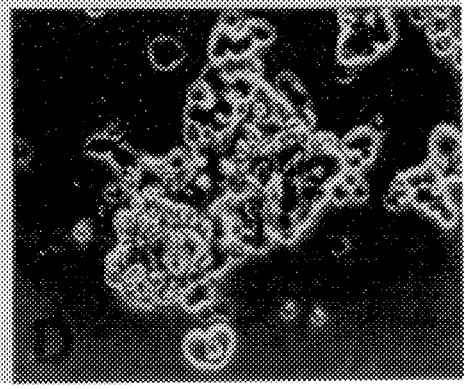
Figure 4A:
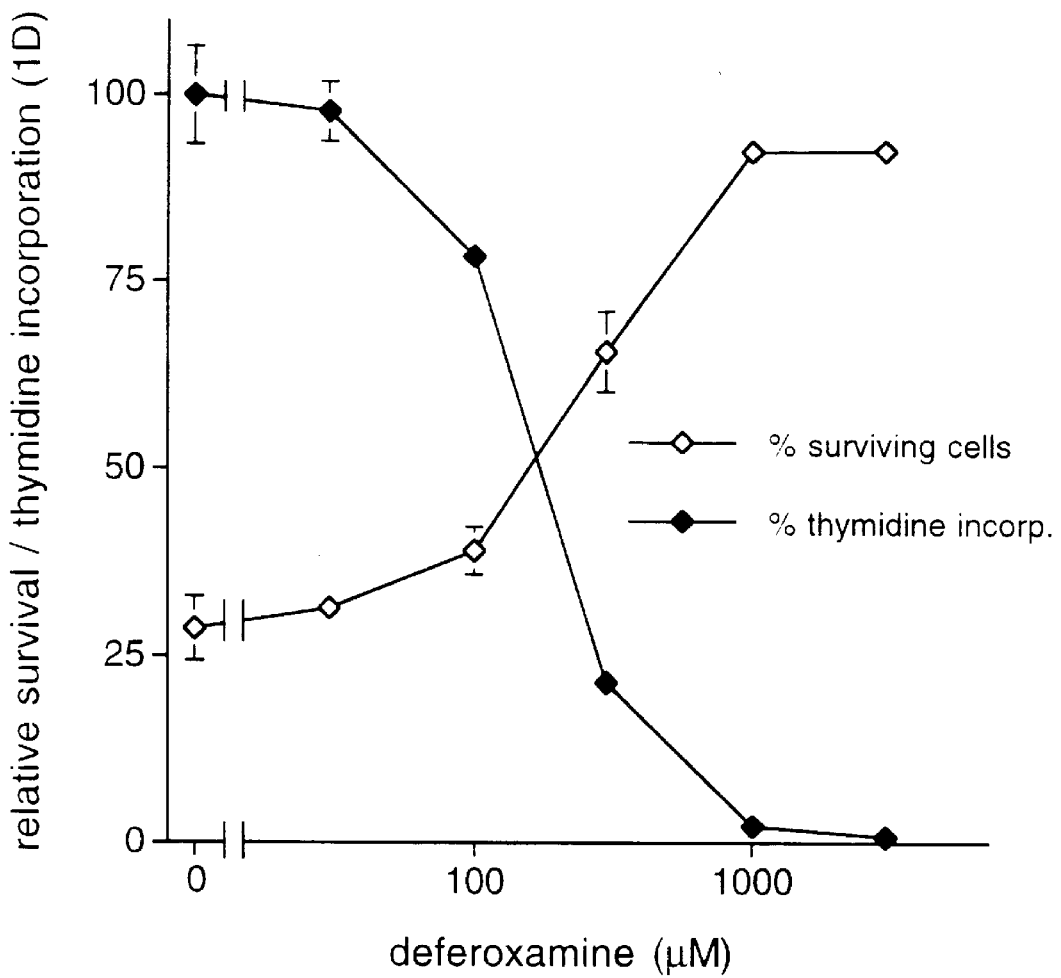
FIGS. 4A, 4B, and 4C show that deferoxamine promotes survival of PC12 cells in serum-free medium and inhibits [$^3$H]-thymidine incorporation. Dose-response relationships for promotion of survival at 1 day and inhibition of thymidine incorporation by deferoxamine (A). For survival studies, cells were pretreated with deferoxamine for 16 hours prior to serum deprivation. Assay of [$^3$H]-thymidine incorporation was conducted following a 24 hour pretreatment with deferoxamine. Time course of survival in serum-free conditions (B). Pretreatment with deferoxamine enhances its protective effect on serum-deprived PC12 cells (C). Pretreated cells were exposed to 1 mM deferoxamine for 16 hours prior to serum-deprivation. $^a$Significantly greater than untreated control (p<0.05). $^b$Significantly less than deferoxamine-pretreated cultures (p<0.05). All data are the mean±SEM of 3 samples.
Figure 4B:
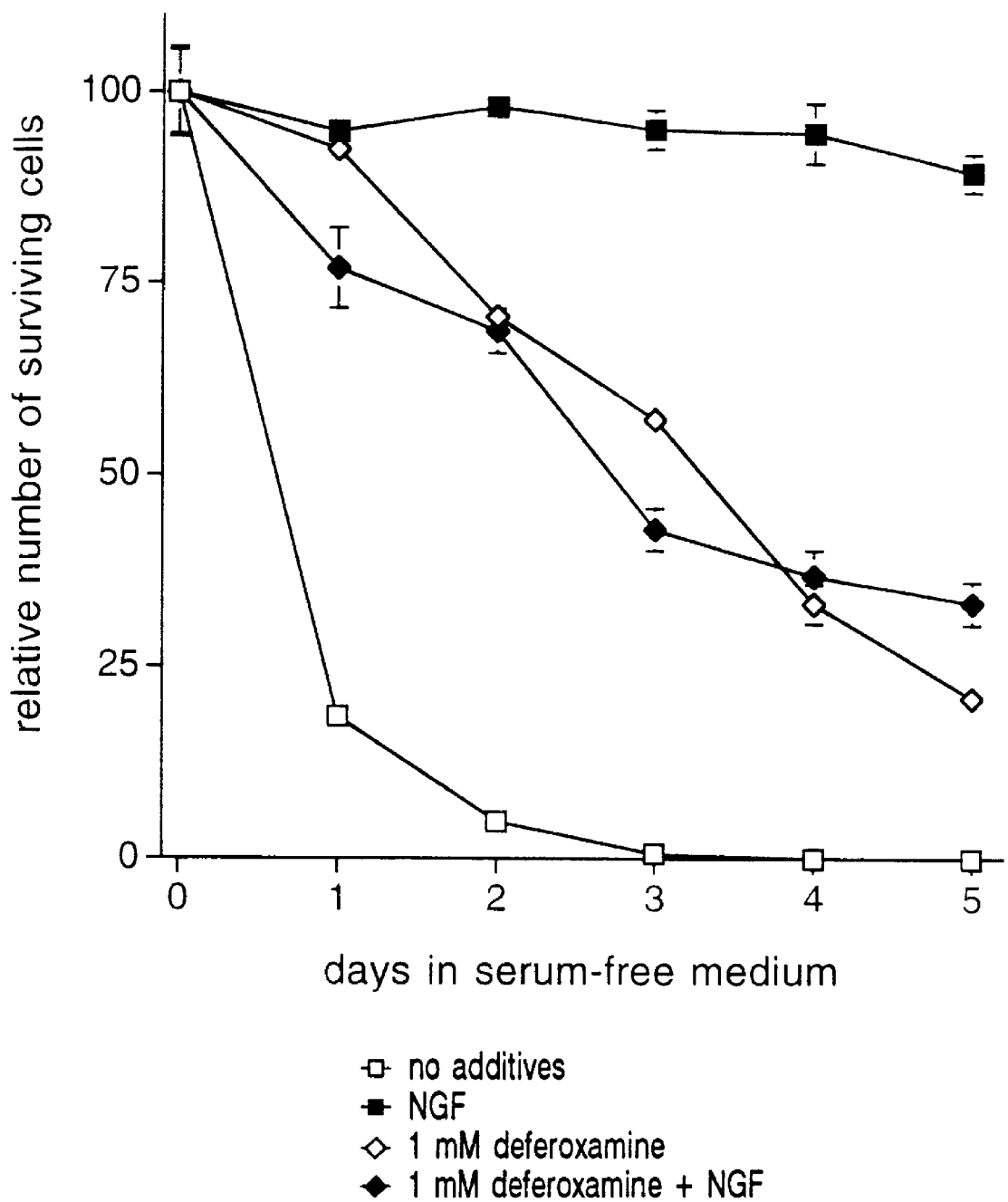
Figure 4C:
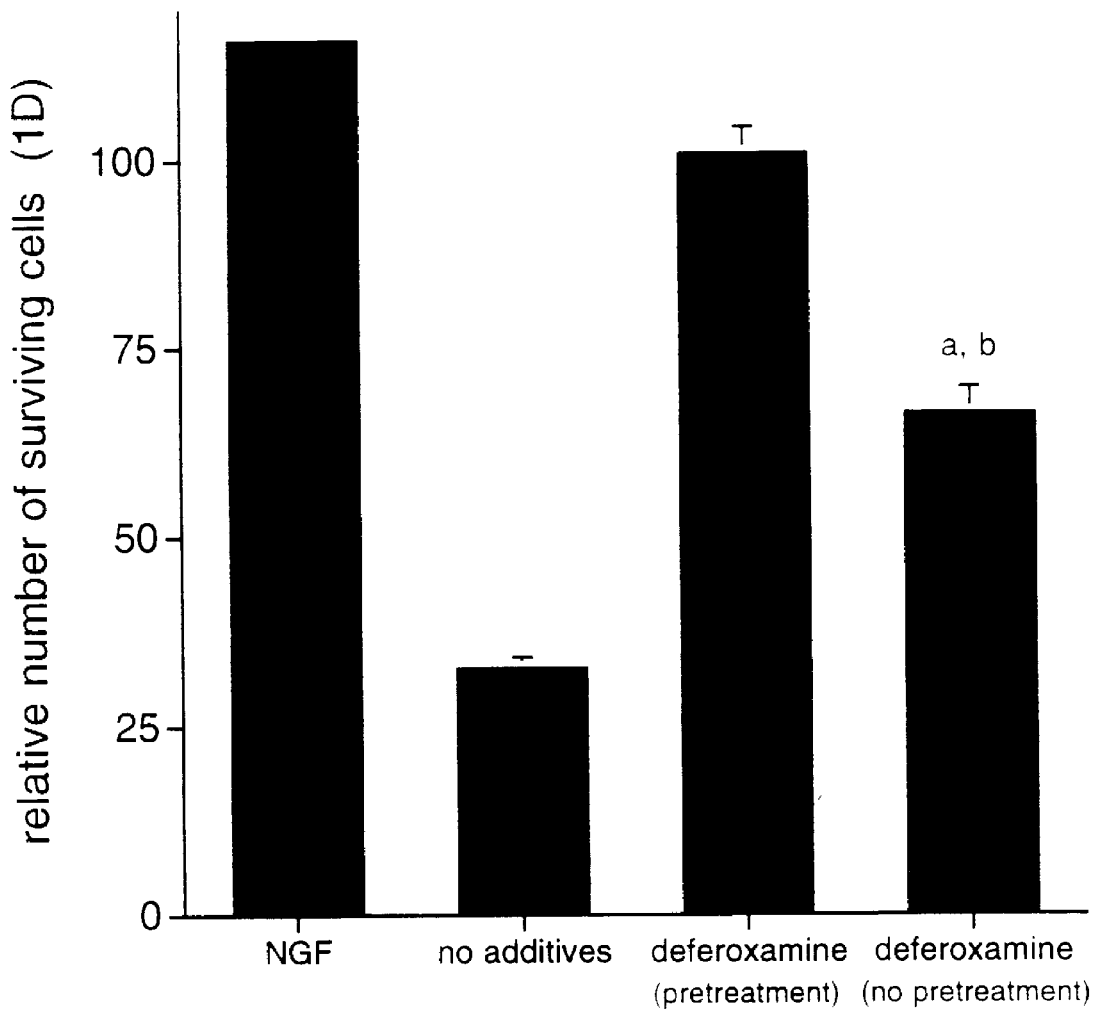

Deferoxamine is thought to block cellular proliferation prior to the G1/S transition by chelating intracellular iron (Brodie et al., 1993). Deferoxamine inhibits DNA synthesis in proliferating PC12 cells in a concentration-dependent fashion (FIG. 4A). Treatment with 1 mM deferoxamine completely blocked thymidine incorporation after 4 hours. As with mimosine, there is a concentration-dependent increase in the survival of serum-deprived PC12 cells, reaching the maximum at 1 mM deferoxamine, the concentration at which DNA synthesis is completely abolished. As shown in FIG. 4B, deferoxamine treatment produces very good short-term survival in this paradigm when compared with untreated cultures. However, after long-term exposure like mimosine, deferoxamine proves toxic to the cells since viability cannot be maintained even when NGF was provided in combination. Overnight pretreatment enhances the protective effect of deferoxamine on serum-deprived PC12 cells (FIG. 4C). Deferoxamine treated cells deprived of serum for one day are shown in FIG. 3D.

Figure 5A:
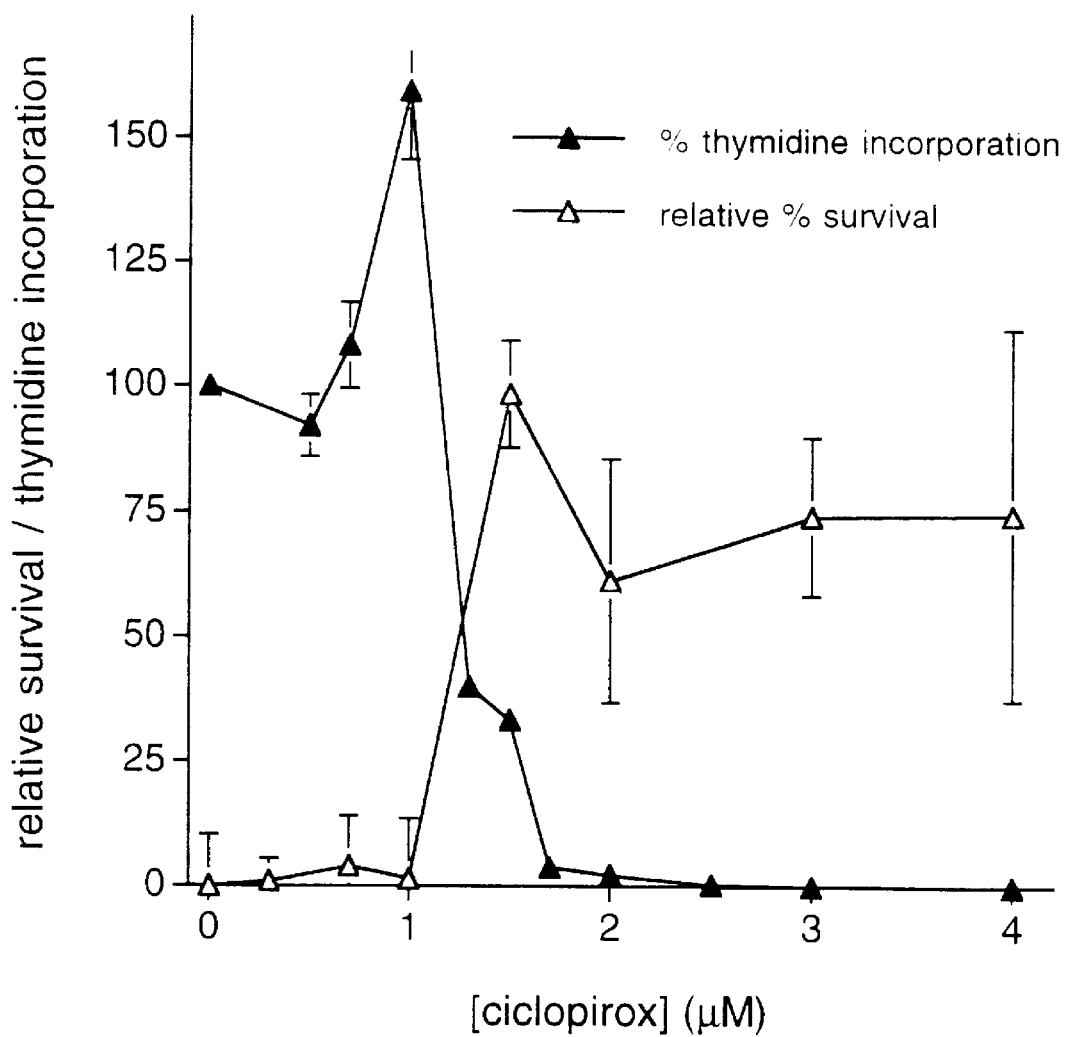
FIGS. 5A and 5B show that ciclopirox promotes survival of PC12 cells in serum-free medium and inhibits [$^3$H]-thymidine incorporation. Dose-response relationships for promotion of survival at 1 day and for inhibition of thymidine incorporation (A). For survival studies, CPX-treated cells were also pretreated with 10 $\mu$M CPX for 16 hours prior to serum deprivation. Survival data are normalized so that the survival without CPX is set at zero. Assay of [$^3$H]-thymidine incorporation was conducted in serum-free conditions with NGF following a 24 hour pretreatment with the indicated concentration of ciclopirox. Time course of survival in serum-free conditions (B). The CPX cultures were pretreated overnight with 10 $\mu$M CPX and replated in serum-free medium containing 3 $\mu$M CPX. All data are the mean±SEM of 3 samples.
Figure 5B:
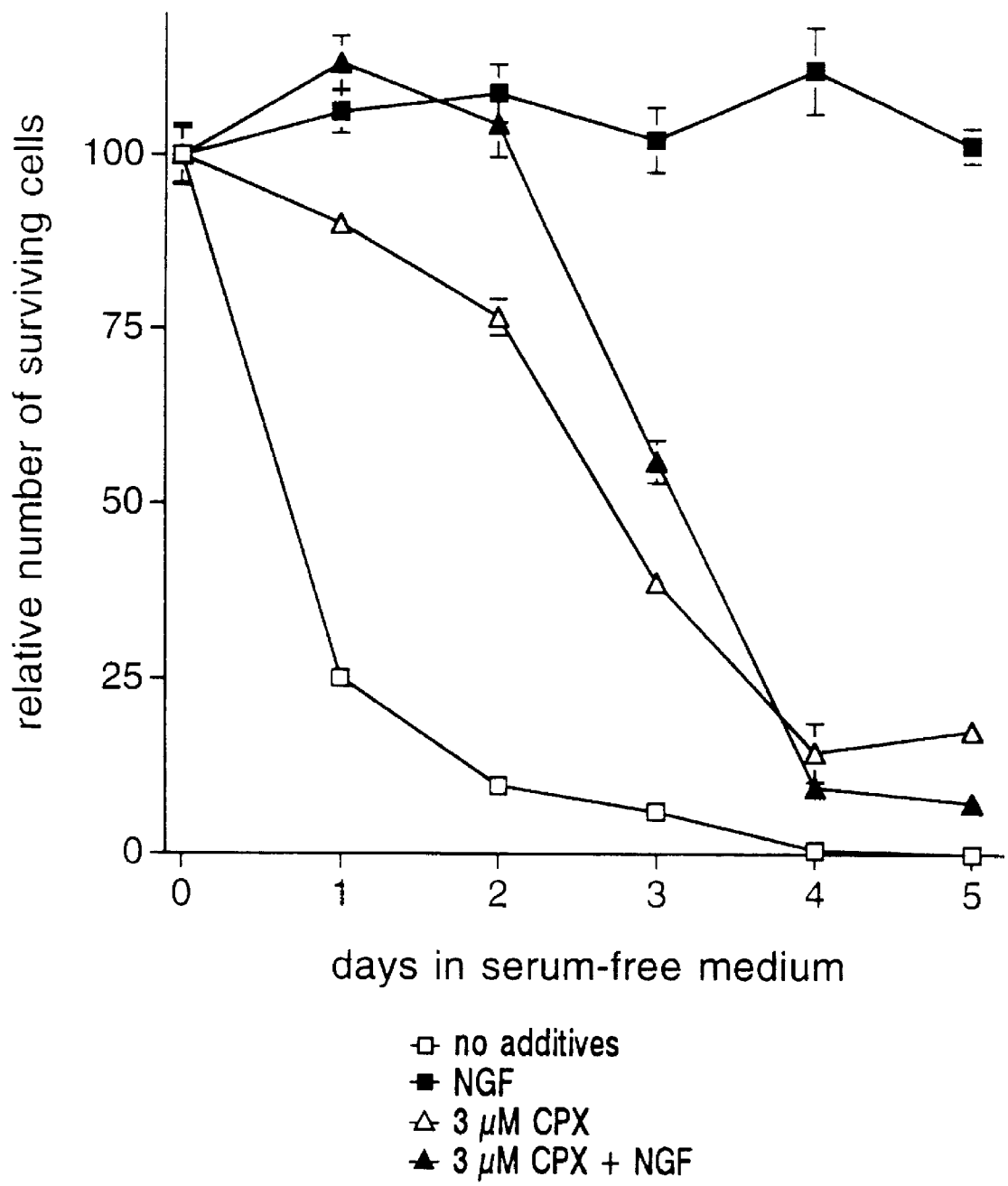

Ciclopirox has been reported to block cells at the same point near the G1/S border as does mimosine, but its mechanism of action is unknown (Hoffman et al., 1991). CPX inhibits thymidine incorporation in PC12 cells with an $IC_{50}$. of approximately 1.5 $\mu$M in serum-free medium, and with an $IC_{50}$ of approximately 5 $\mu$M in medium containing 15% serum. In serum-free medium, there was a reproducible increase in [$^3$H]-thymidine incorporation with 1 $\mu$M CPX before the steep decline; at 2 $\mu$M CPX, inhibition of DNA synthesis was virtually complete (FIG. 5A). Following overnight pretreatment of PC12 cells growing in serum-containing medium with 10 $\mu$M CPX, the drug was able to promote near complete survival 24 hours after serum-deprivation, and did so at concentrations similar to those required to inhibit [$^3$H]-thymidine incorporation (FIG. 5A). As with mimosine and deferoxamine, it was necessary to pretreat cells with CPX prior to serum-deprivation to obtain maximal survival. FIG. 5B depicts the time course of the effects of CPX treatment on survival in this paradigm. Survival was very good up to two days after serum deprivation (>75% survival). However, CPX was unable to maintain good long-term survival. This appeared due to toxicity of the drug, because even when NGF was present in combination with CPX there was a similar loss of cell viability.

Figure 6A:
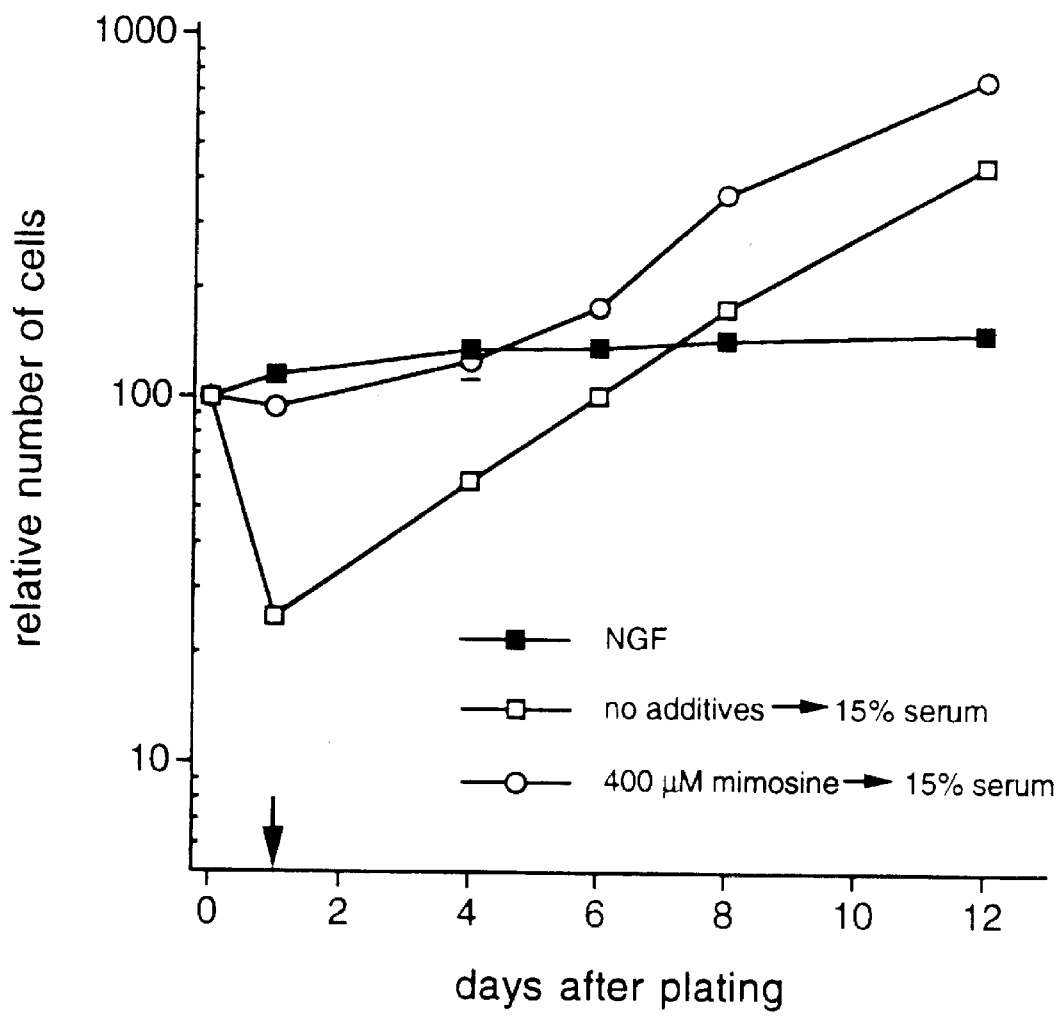
FIGS. 6A, 6B, and 6C show viability of cells cultured with G1 blockers. Reversibility (A). Cells were cultured for 24 hours in serum-free medium with or without 400 $\mu$M mimosine and then with medium containing 15% serum. Cells maintained continuously in serum-free medium containing NGF are shown for reference. Cell numbers were determined at the indicated times and are expressed on a semi-log plot relative to the number initially plated (day 0). Metabolism (B). Replicate cultures were maintained for 24 hours in serum-free medium with NGF, no additive, 400 $\mu$M mimosine (MIMO), 1 mM deferoxamine (DF) or 3 $\mu$M ciclopirox (CPX) and then assessed for Alamar Blue metabolism as described in Materials and Methods. The data for each treatment group are normalized to the signal obtained from replicate cultures immediately following plating. Protein synthesis (C). Cultures of PC12 cells and sympathetic neurons were pretreated with the indicated concentrations of mimosine for 4 hours and then incubated for 16 additional hours with mimosine and [$^3$H]-leucine. Cultures were then assayed for [$^3$H]-leucine incorporation as described in Materials and Methods. Data are expressed relative to untreated control cultures. All data are the mean±SEM of 3 samples.
Figure 6B:
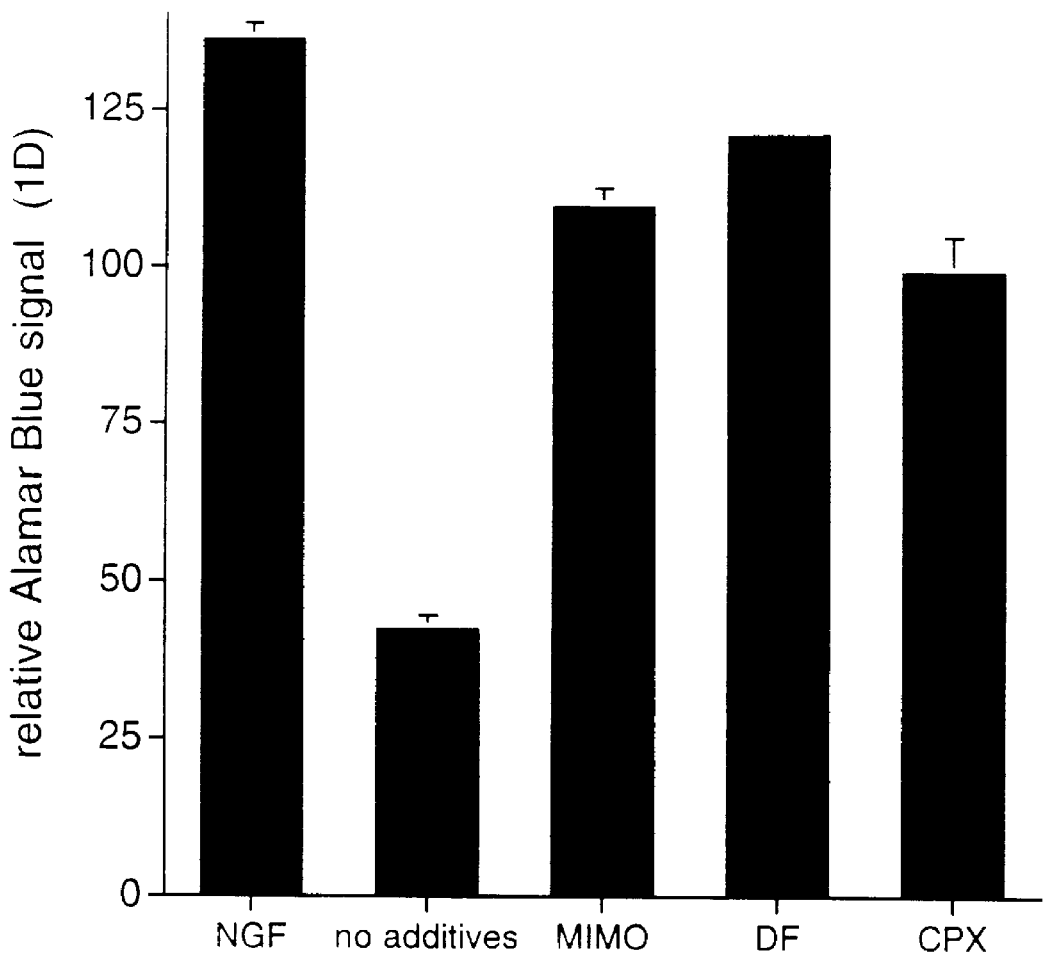

Several independent methods in addition to cell counting were used to confirm the viability of the cells treated with the G1/S blockers. These are presented in FIGS. 6A, 6B, and 6C. Cultures were maintained in serum-free medium with mimosine for one day and then washed free of the drug and returned to medium containing 15% serum. Under these conditions following a lag phase for the cells that had been maintained by mimosine, proliferation re-commenced, thus providing a clear indication of viability (FIG. 6A). The lag phase presumably reflects the time required for the drug to be cleared from the cells. We also utilized the vital indicator Alamar Blue, a dye which is reduced by living cells, to examine the extent of cell survival. The data in FIG. 6B indicate that by this criterion all three G1/S blockers maintained full cell viability in serum-free medium. In addition, nuclear morphology of serum-deprived PC12 cells (exposed to no additive, NGF, ciclopirox, mimosine or deferoxamine for 24 hours) was visualized using the stain Hoechst 33342. Quantitation of normal and pyknotic nuclei provided similar results to those achieved by counting of intact nuclei. In this assay the proportions of cells with pyknotic nuclei (n=100–200 nuclei per treatment) were 56%, no additive; 9%, NGF; 9%, ciclopirox; 11% deferoxamine; and 11% mimosine.

Figure 6C:
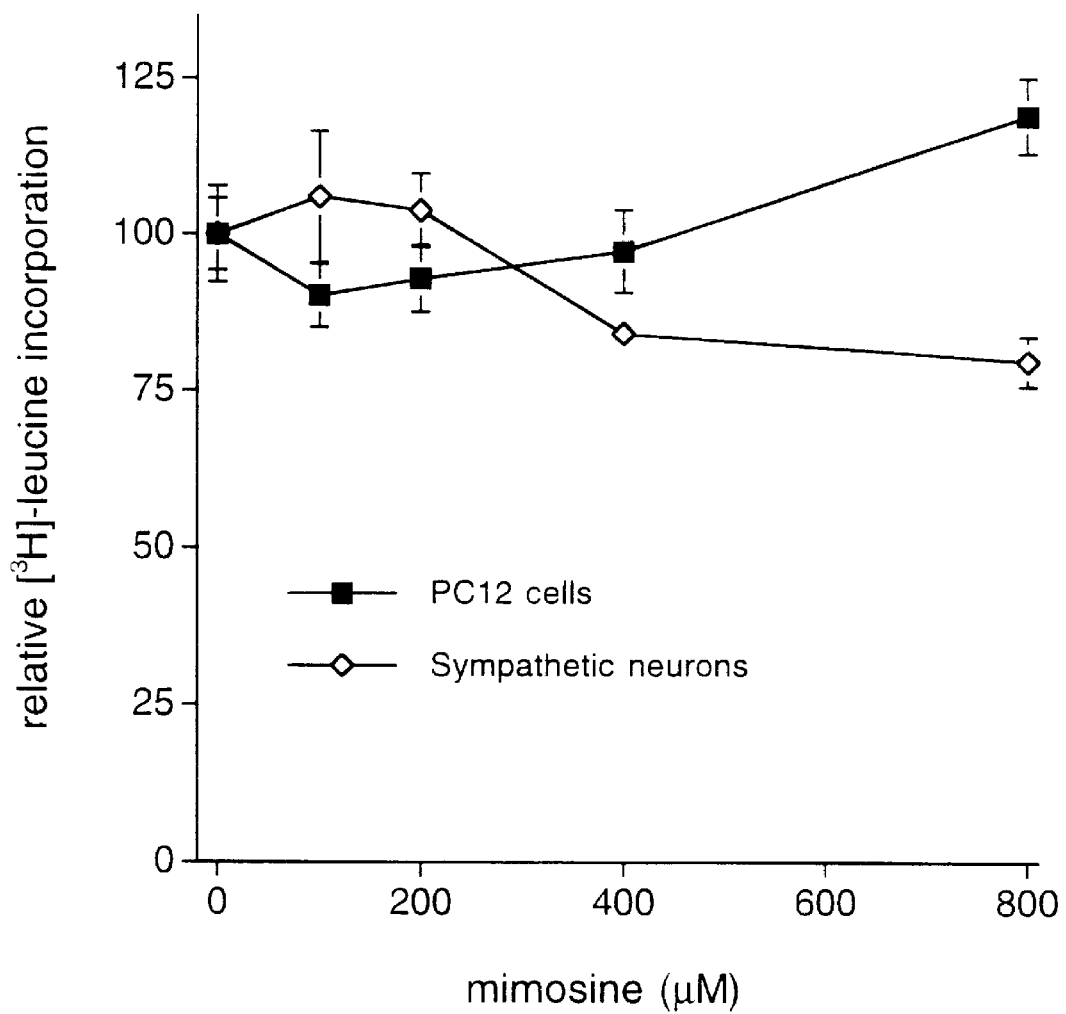

Since mimosine is an amino acid and was used at relatively high concentrations, we determined if this agent might prevent cell death by interfering with protein synthesis. The data in FIG. 6C shows that mimosine does not inhibit protein synthesis by more than 15–20% in either PC12 cells or primary sympathetic neurons at concentrations up to 800 $\mu$M. Martin et al. (1992) reported that cell death was prevented by cycloheximide in NGF-deprived sympathetic neuron cultures, only when protein synthesis was blocked by 80% or greater. Thus, mimosine does not promote survival by inhibiting protein synthesis.

Figure 7A:
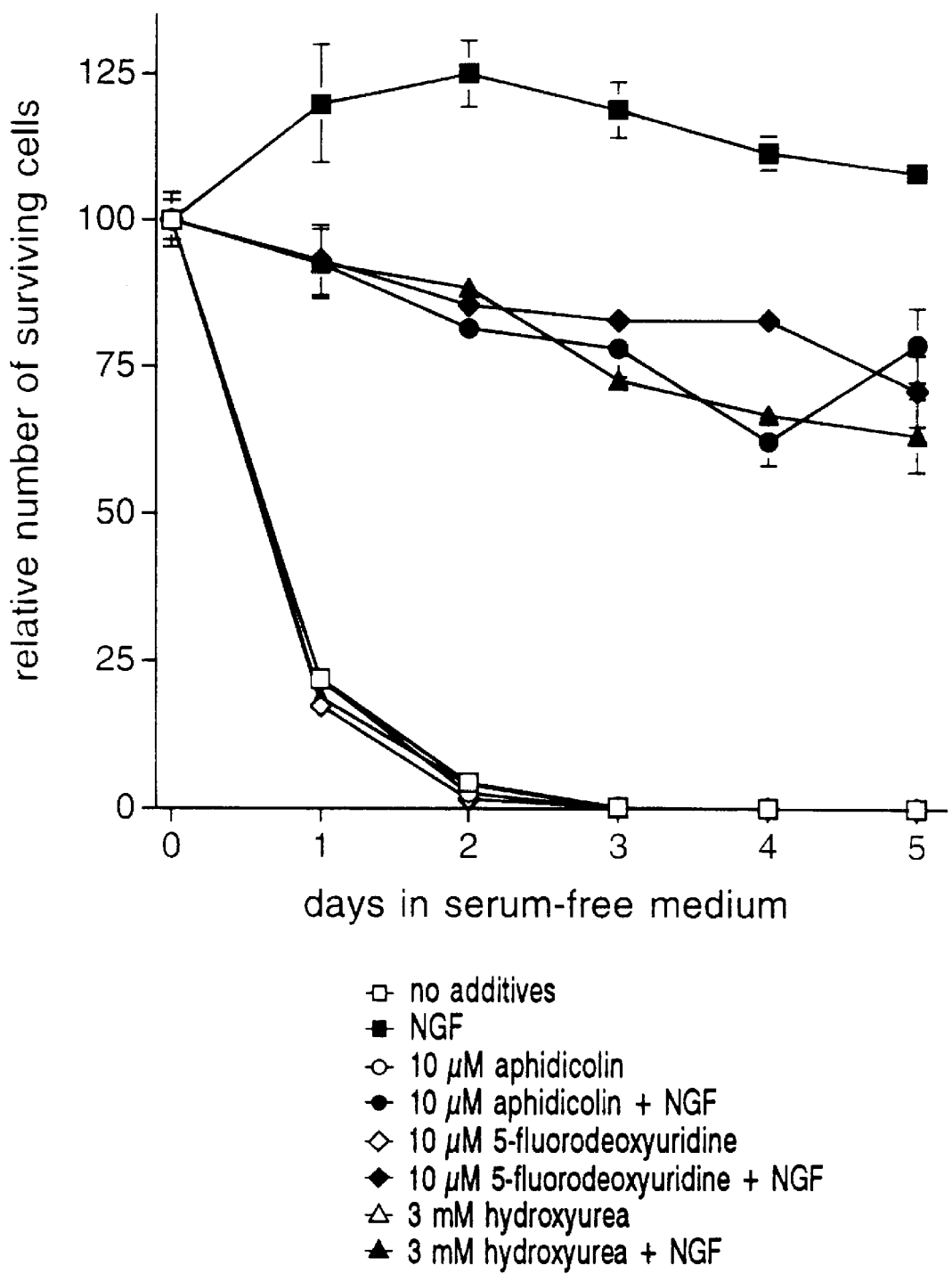
FIGS. 7A, 7B, 7C, and 7D show that neither S-, G2- nor M-phase blockers prevent the death of naive PC12 cells in serum-free conditions or of neuronal PC12 cells following NGF withdrawal. Serum-deprived naive PC12 cells. Cultures were pretreated with the indicated agent for 16 hours prior to serum deprivation. DNA synthesis inhibitors (A). G2 and M-phase blockers (B). NGF-deprived neuronally-differentiated PC12 cells. PC12 cells were neuronally differentiated by treatment with NGF for 10–14 days in serum-free medium. PC12 cells were washed free of NGF and replated in the presence of the indicated agent. Cultures were not pretreated with agents prior to NGF withdrawal. DNA synthesis inhibitors (C). G2 and M-phase blockers, 2-days after NGF withdrawal (D). Cell survival data are expressed relative to the number initially plated. All data are the mean±SEM of 3 samples.

Neither S-, G2- nor M-phase blockers prevent the death of serum-deprived naive PC12 cells The three S-phase blockers chosen for these studies inhibit distinct enzymes necessary for DNA synthesis. Aphidicolin inhibits DNA polymerase $\alpha$ (Ikegami et al., 1978), 5-fluorodeoxyuridine inhibits thymidylate synthetase (Jackson, 1978) and hydroxyurea blocks ribonucleotide reductase (Adams and Lindsay, 1967). The concentrations of aphidicolin, 5-fluorodeoxyuridine and hydroxyurea we used were 10 $\mu$M, 10 $\mu$M and 3 mM respectively. At these concentrations DNA synthesis was inhibited greater than 95% after 3 hours. However, none of the S-phase blockers was able to prevent the death of serum-deprived PC12 cells (FIG. 7A). These blockers were ineffective regardless of the length of the pretreatment period (up to three days prior to serum withdrawal, data not shown). Addition of NGF to the cultures maintained their survival in the presence of the inhibitors, indicating that the drugs themselves did not cause cell death.

Figure 7B:
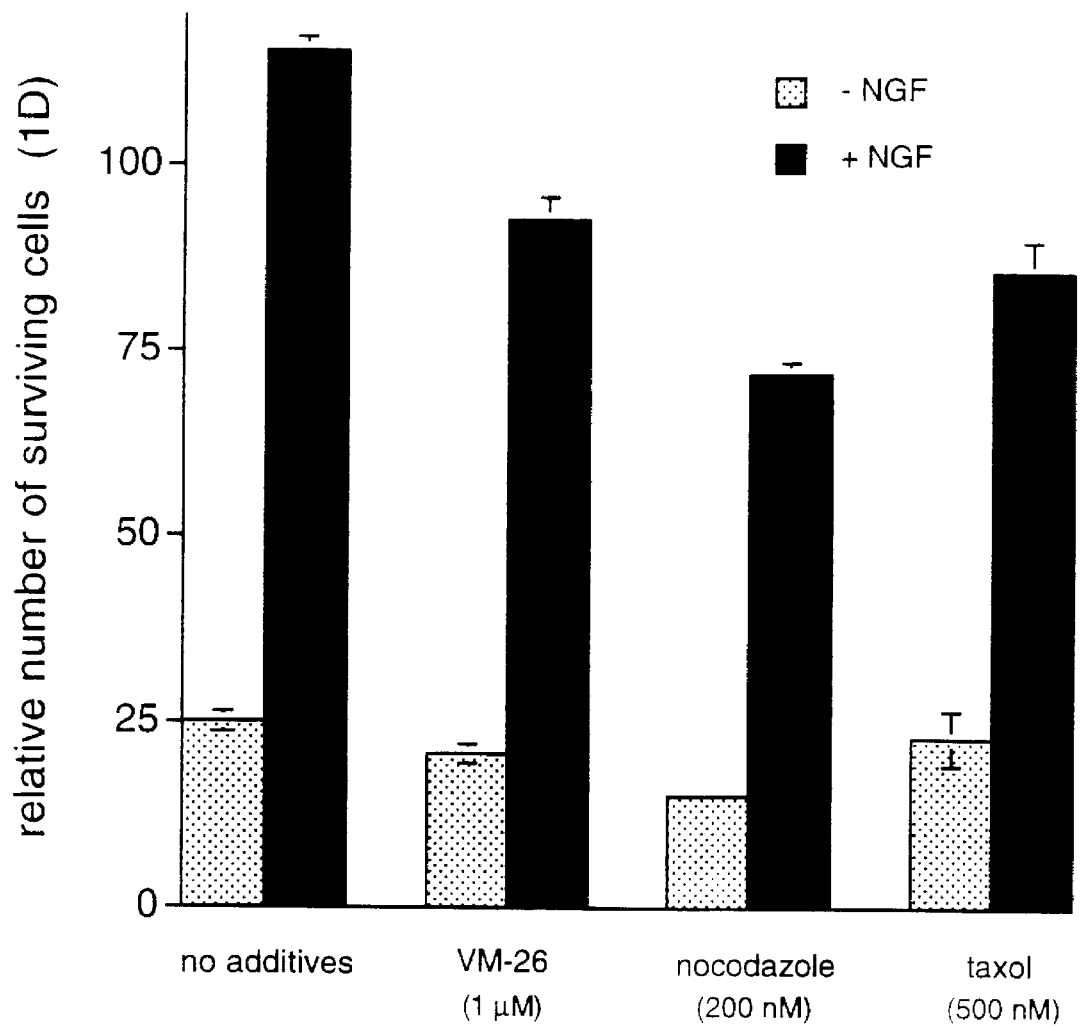

The topoisomerase inhibitor VM-26 blocks cells in the G2 phase of the cell cycle (Roberge et al., 1990; Chen and Beck, 1993). Nocodazole and taxol, agents which respectively inhibit and stabilize polymerization of microtubules, block cells in mitosis (Schiff et al., 1979; Wilson and Jordan, 1994). Each of these agents blocks DNA synthesis, but in contrast to the other agents used here, the M-phase inhibitors required two days of pretreatment before causing complete inhibition of thymidine incorporation. This was to be expected since the PC12 cell cycle lasts approximately 2.5 days, with M-phase taking only a small fraction of that. Preliminary investigations revealed that the concentrations of VM-26, nocodazole and taxol required to block DNA synthesis were 1 $\mu$M, 200 nM and 500 nM respectively. As with the S-phase blockers, G2- and mitotic inhibitors failed to prevent the death of PC12 cells following serum withdrawal (FIG. 7B). These blockers were ineffective regardless of the length of pretreatment (up to three days, data not shown). In this paradigm, NGF substantially prevented the death of PC12 cells in the presence of the inhibitors. The capacity of NGF to rescue cells blocked in S, G2 or M contrasts with the suggestion that NGF actions might be limited to a particular phase of the cell cycle (Rudkin et al., 1989).

Neuronally-Differentiated PC12 Cells

Figure 8A:
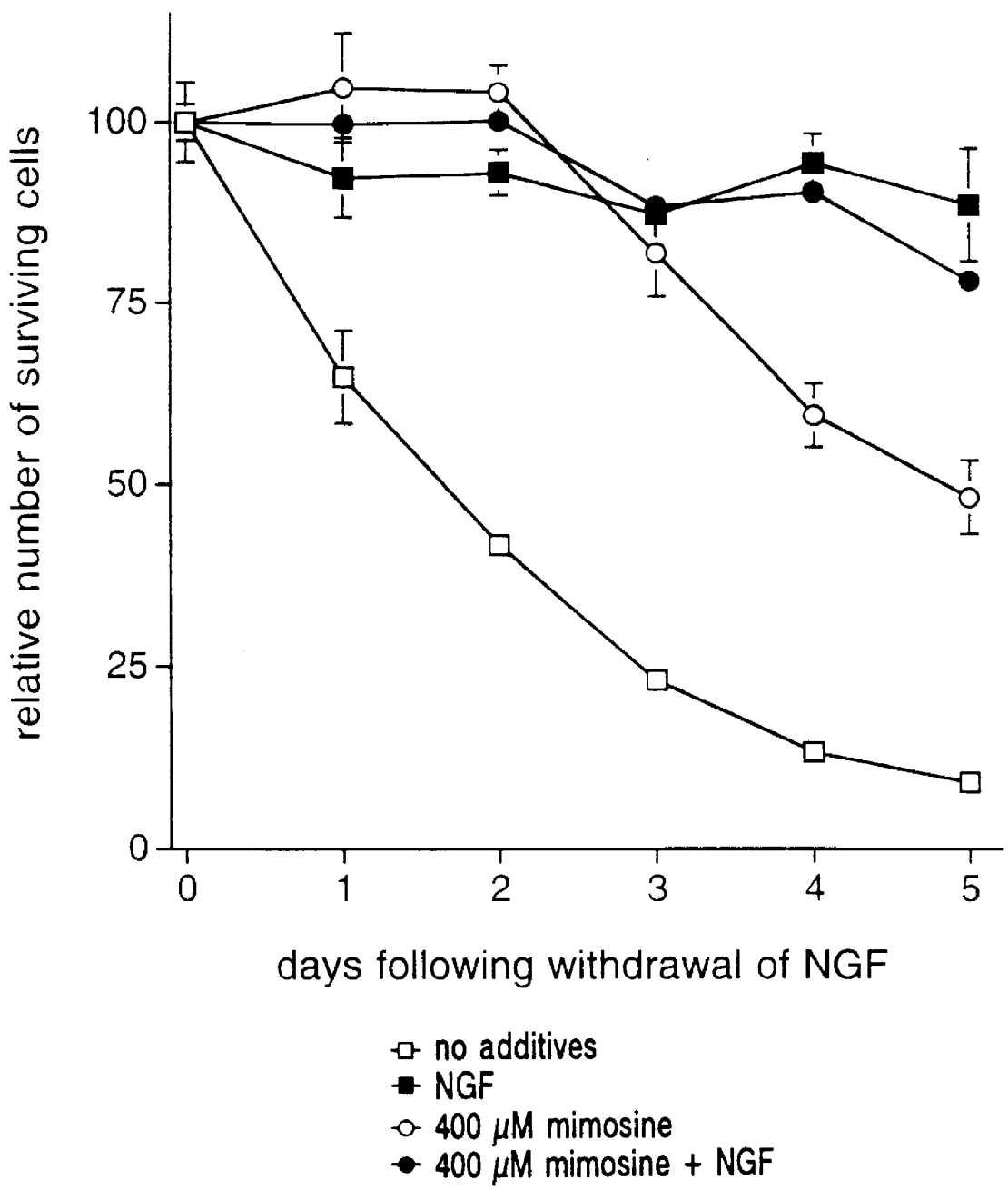
FIGS. 8A, 8B, and 8C show that G1 blockers prevent the death of neuronally-differentiated PC12 cells in serum-free medium following removal of NGF. PC12 cells were differentiated by treatment with NGF for 10–14 days in serum-free medium. PC12 cells were washed free of NGF and replated in the presence of the indicated agent. Cultures were not pretreated with agents prior to NGF withdrawal. Effects of mimosine on NGF-primed PC12 cell survival following removal of NGF in serum-free medium (A). Effects of deferoxamine on NGF-primed PC12 cell survival following removal of NGF in serum-free medium (B). Effects of ciclopirox on NGF-primed PC12 cell survival following removal of NGF in serum-free medium (C). Cell survival data are expressed relative to the number initially plated. All data are the mean±SEM of 3 samples.
Figure 8B:
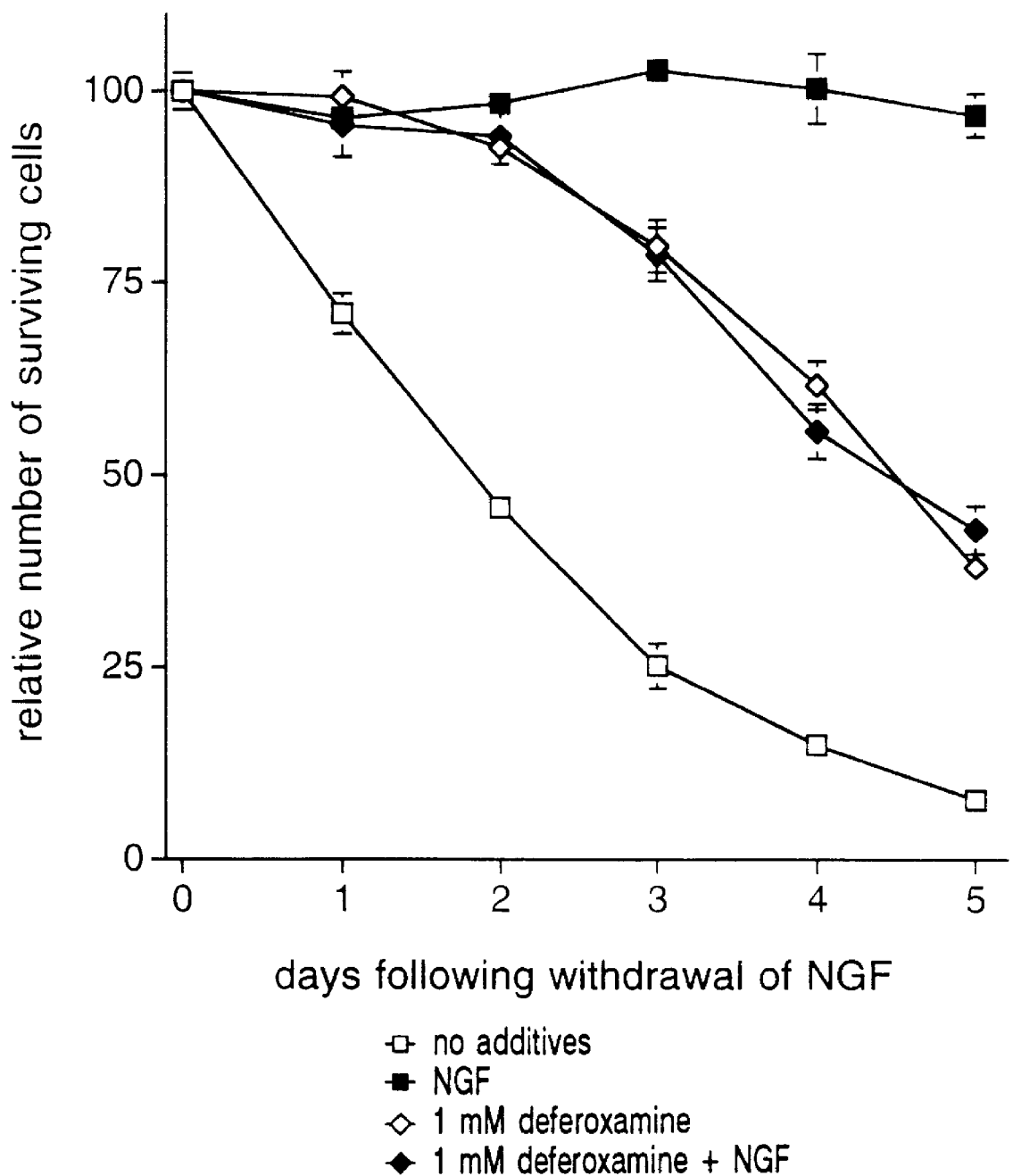
Figure 8C:
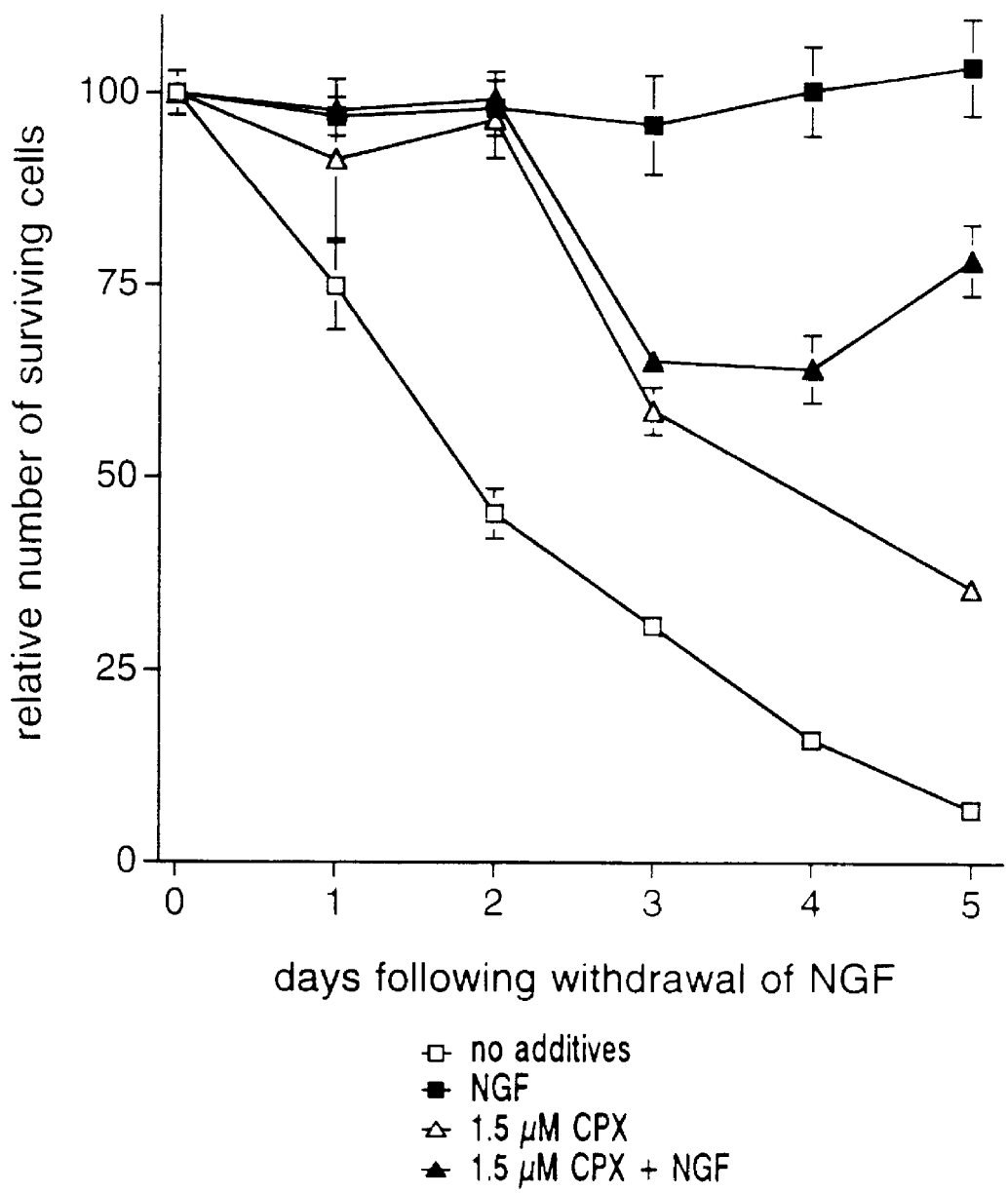

Mimosine, deferoxamine and ciclopirox prevent the death of neuronal PC12 cells following removal of NGF Next, the cell cycle blockers' ability to prevent the death of PC12 cells that were neuronally differentiated by long term treatment with NGF in serum-free medium and then deprived of the factor was tested. After several days in serum-free medium with NGF, PC12 cells stop dividing and acquire many of the phenotypic properties of sympathetic neurons (Greene and Tischler, 1982). Serum-deprived neuronal PC12 cells, like sympathetic neurons, die after NGF withdrawal, with roughly 50–60% of the cells dead after two days. Addition of 400 $\mu$M mimosine, 1 mM deferoxamine or 1.5 $\mu$M CPX to cultures of neuronal PC12 cells after the cells were washed free of NGF resulted in near complete survival for up to two days, and approximately 80% survival at three days. In contrast, only 25% of untreated cells remained viable at the latter time (FIGS. 8A, 8B, and 8C). After two to three days in the absence of NGF, there was a gradual decrease in the number of cells maintained by the three drugs. This appeared to be attributable to the toxic effects of these agents (FIGS. 8A, 8B, and 8C). Unlike naive PC12 cells deprived of serum, it was not necessary to pretreat neuronal PC12 cells with mimosine or deferoxamine prior to NGF withdrawal in order to obtain complete survival. In the absence of NGF, these three agents did not promote neurite regeneration, nor did they prevent this process in the presence of NGF (not shown).

Figure 7C:
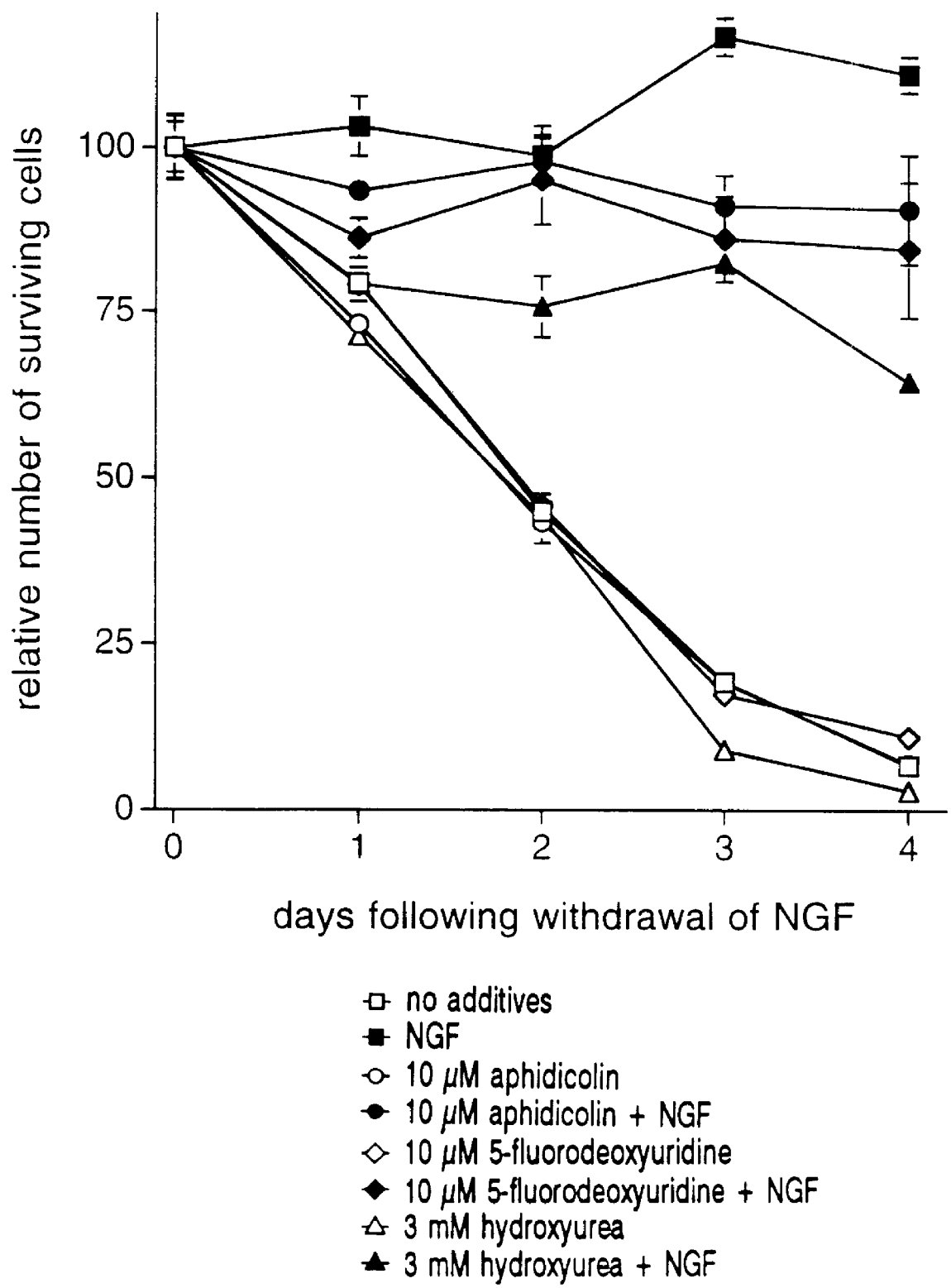
Figure 7D:
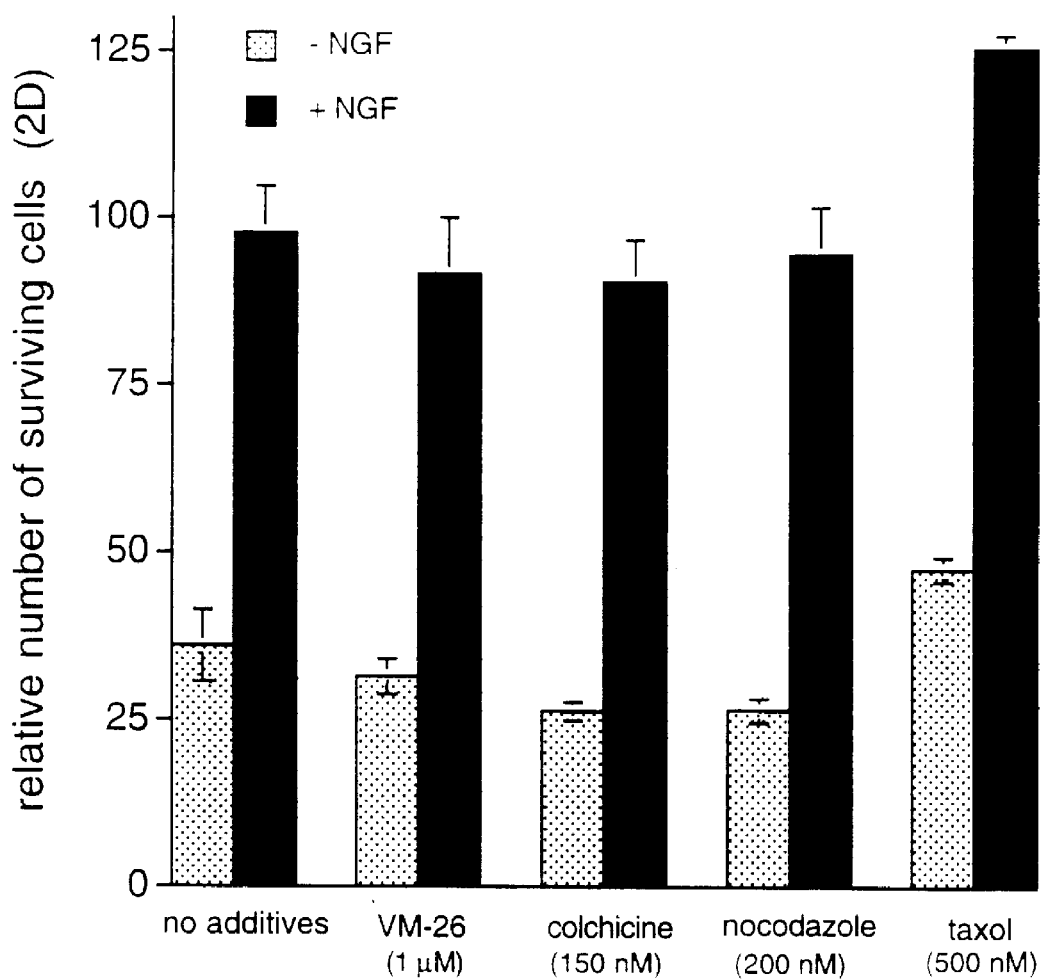

Neither S-, G2- nor M-phase blockers prevent the death of neuronal PC12 cells following the removal of NGF The ability of the other cell cycle blockers to prevent the death of NGF-deprived neuronal PC12 cells was tested. The data in FIG. 7C and 7D show that neither S-, G2- nor M-phase blockers rescue these cell from death. Cells treated with S-phase blockers die at the same rate as untreated controls, while cells that received NGF along with the inhibitor were largely protected (FIG. 7C). FIG. 7D shows basically the same outcome with G2 and M-phase inhibitors. Two days following NGF removal, roughly the same fraction of cells died despite the presence of these agents. NGF rescued the cells from death under all conditions demonstrating that the inhibitors themselves were not toxic in this paradigm. None of the inhibitors were able to prevent cell death even when the cultures were pretreated up to three days prior to NGF withdrawal (data not shown).

Primary Sympathetic Neurons

Figure 9A:
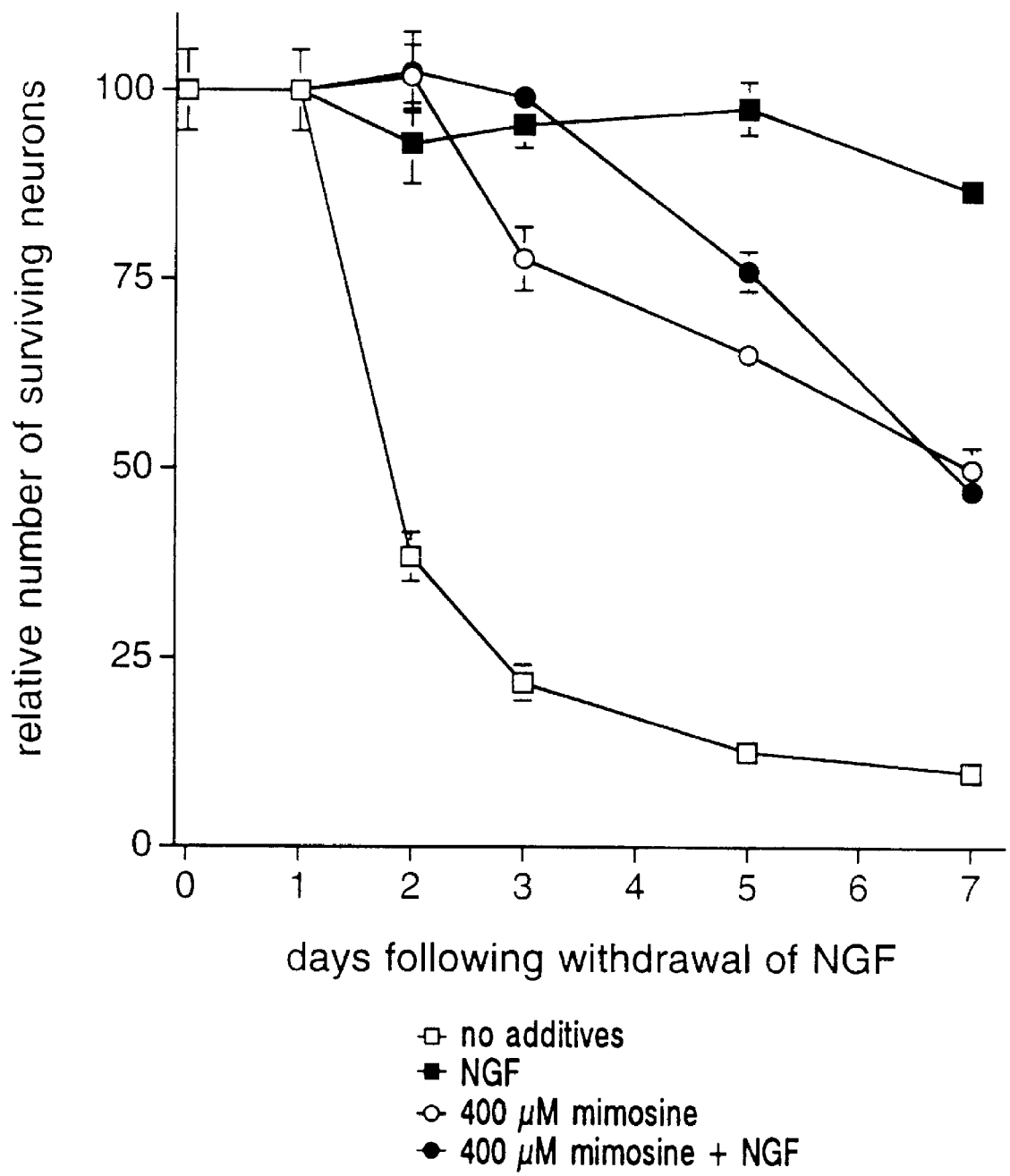
FIGS. 9A, 9B, 9C, 9D and 9E show that G1 blockers suppress the death of primary sympathetic neurons following removal of NGF, whereas S-, G2- and M-phase blockers do not. Neurons were cultured in the presence of NGF for 6 days prior to its withdrawal (only for 3 days in the CPX experiment, see Materials and Methods). Cultures were not pretreated with agents prior to NGF withdrawal. Effects of mimosine on survival of sympathetic neurons following removal of NGF (A). Effects of deferoxamine on survival of sympathetic neurons following removal of NGF (B). Effects of ciclopirox on survival of sympathetic neurons following removal of NGF (C). Readdition of NGF to cultures maintained without the NGF and with or without G1/S blockers for 36 hours (D). Neurons were deprived of NGF as described above; 36 hours (arrow) after NGF withdrawal with or without exposure to the G1/S blockers the cultures were washed once and NGF added back in medium lacking the blockers. Neurons deprived of NGF and replaced with medium containing. S-, G2- and M-phase blockers fail to prevent the death of primary sympathetic neurons following removal of NGF, 3-days after NGF withdrawal (E). Cell survival data are expressed relative to the number present following removal of NGF. All data are the mean±SEM of 3 samples.
Figure 9B:
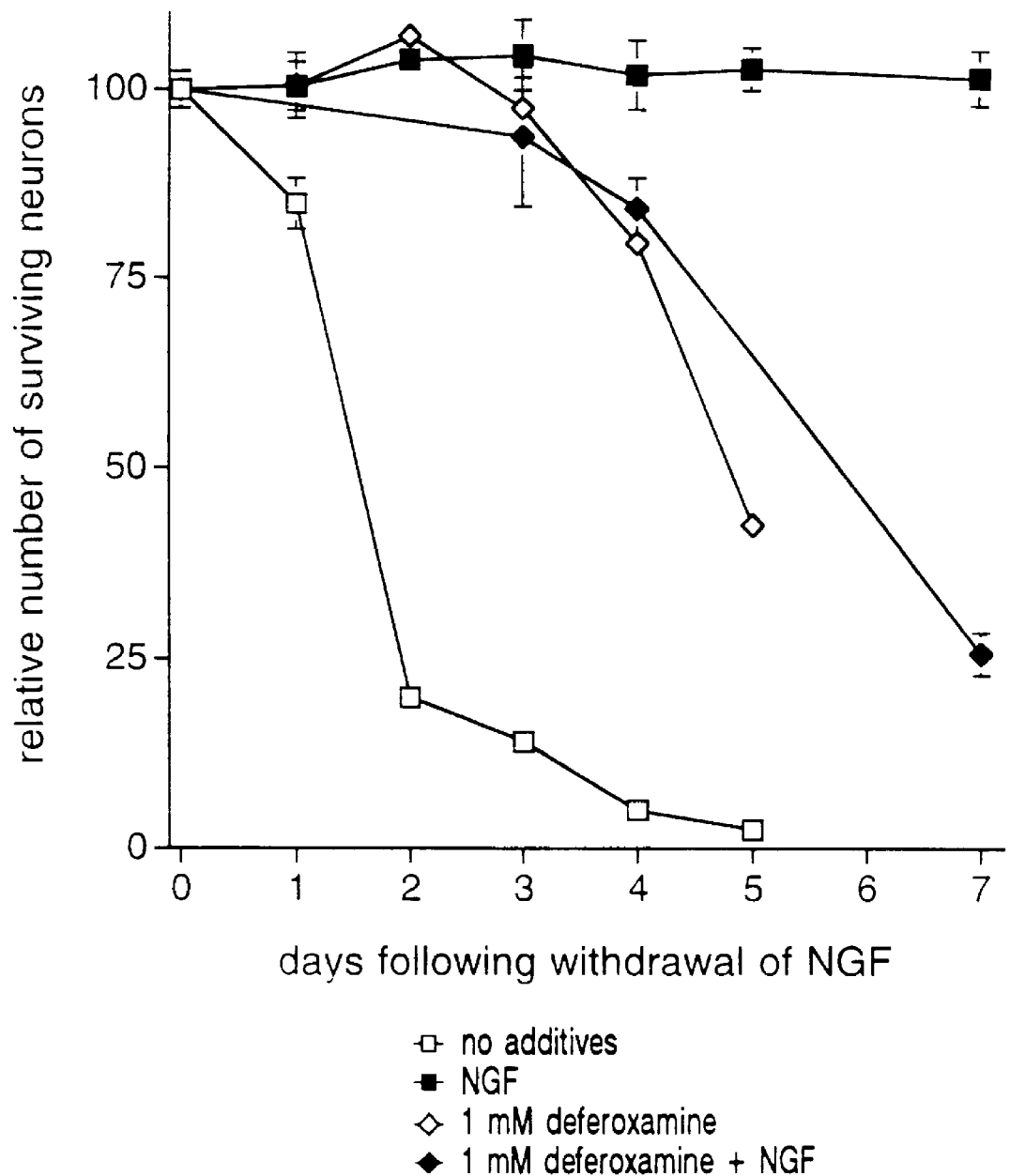
Figure 9C:
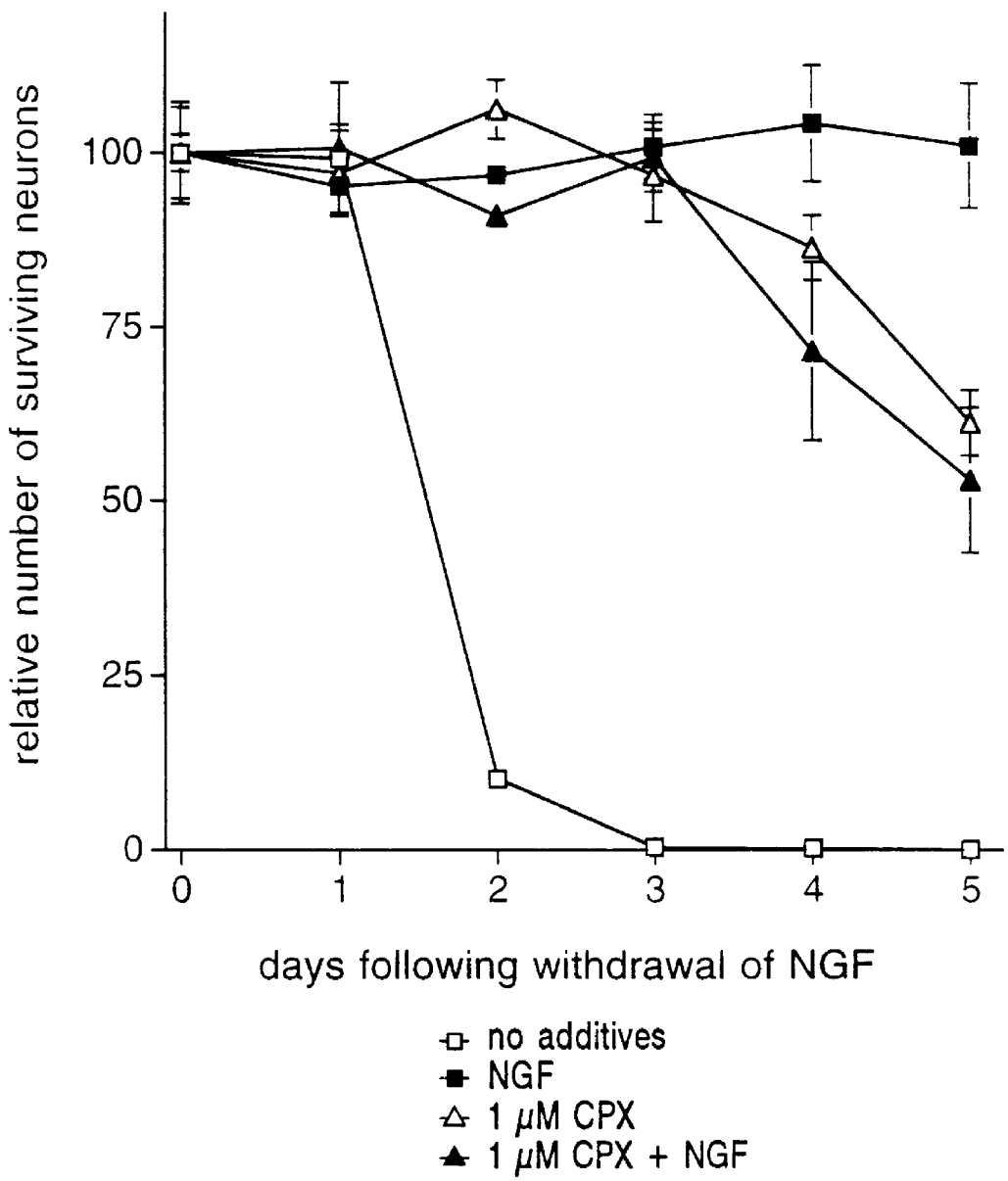

G1 blockers mimosine, deferoxamine and ciclopirox prevent the death of sympathetic neurons following removal of NGF, whereas S, G2 and M-phase blockers do not The results with neuronal PC12 cells indicate that mimosine, deferoxamine and CPX prevent death of cells that are nonmitotic at the time of NGF withdrawal. To extend these observations to a post-mitotic neuronal model, the effects of cell cycle blockers on NGF-deprived sympathetic neurons was examined next. In this paradigm, sympathetic neurons from two day old rats were cultured in the presence of NGF for six days (or three days in the CPX experiments) and then deprived of the factor. Under these conditions, approximately 50–60% of the neurons die within 48 hours and virtually all die by five days. Addition of mimosine, deferoxamine or CPX to cultures of sympathetic neurons immediately following NGF withdrawal rescued them from death (FIGS. 9A, 9B, 9C, 9D, and 9D and FIGS. 10A, 10B, 10C, 10D, 10E, and 10F). The dose-response relationships for neuronal survival (data not shown) correlated well with those observed for naive PC12 cell survival following serum deprivation (see FIGS. 2A, 4A and 5A), consistent with the possibility that the mechanism of rescue may be similar in the two systems. After three days of deprivation, approximately 80% of the mimosine-treated neurons, 90% of the deferoxamine-treated neurons and >95% of the CPX-treated neurons retained a phase-bright, viable appearance compared with less than 25% of their untreated counterparts. Although the neurons in cultures treated with these agents showed loss of somal volume, they maintained their neurite network in the absence of NGF in contrast to the dying, untreated controls (FIGS. 10A, 10B, 10C, 10D, 10E, and 10F). As shown in FIG. 6C the effect of mimosine was not due to suppression of protein synthesis. Although both agents maintained survival, they did not promote somatic hypertrophy as did NGF (FIG. 10B). viability of the neurons began to decline after three days in the presence of either agent. As with PC12 cells, this appeared due to a long-term toxic action of these agents because the cells die even if NGF is present in combination with these drugs (FIGS. 9A, 9B, and 9C) This toxicity was concentration-dependent.

Figure 9D:
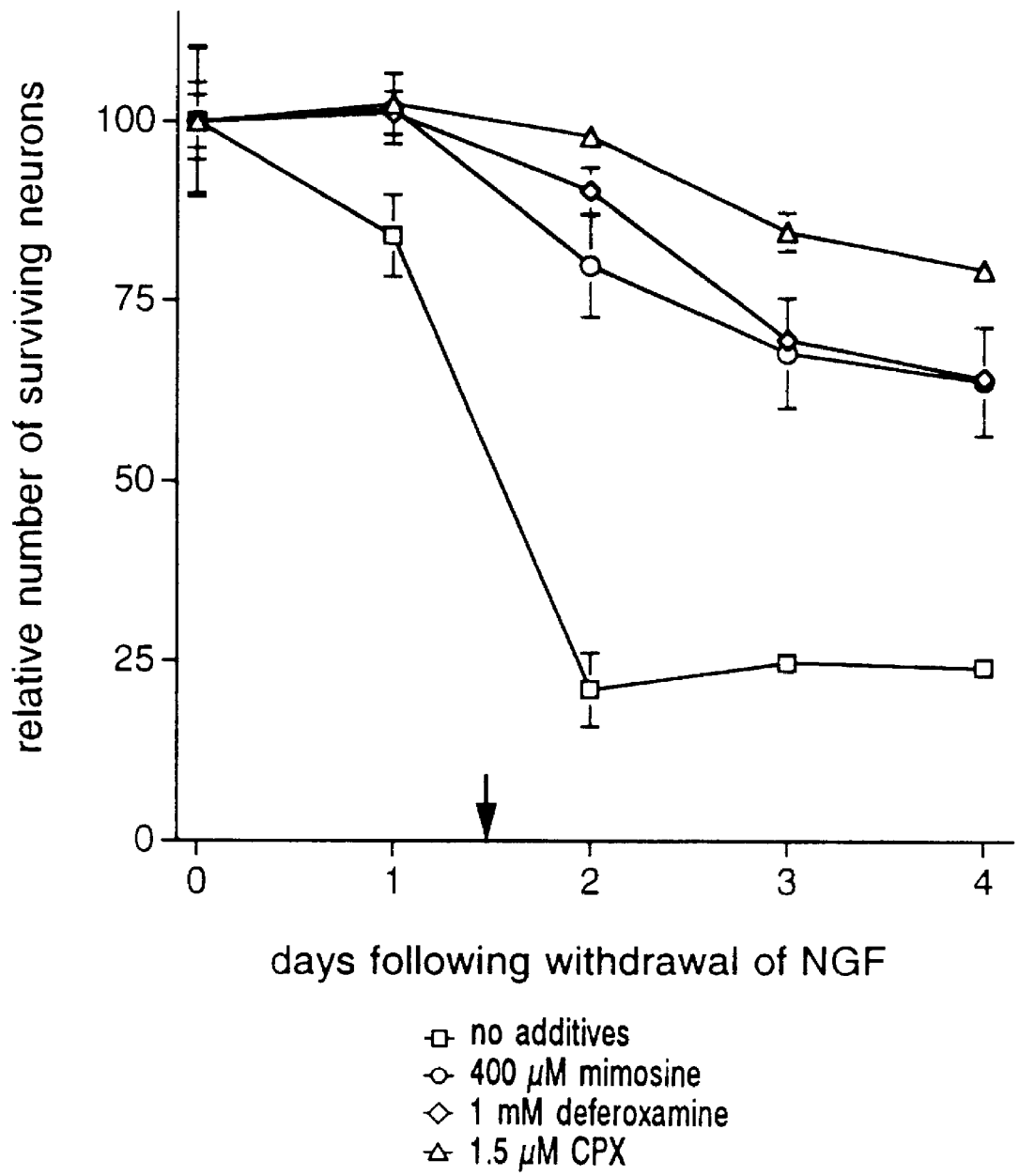

To verify that the neurons maintained by the G1/S blockers were indeed viable, the drugs were removed and NGF was re-added to cultures. As observed by microscopic inspection, removal of the blockers and readdition of NGF was accompanied by the return of somatic hypertrophy and by renewed outgrowth of the neuritic network. Moreover, as shown in FIG. 9D, quantification revealed that the majority of neurons initially maintained by the blockers continued to survive with NGF.

Figure 9E:
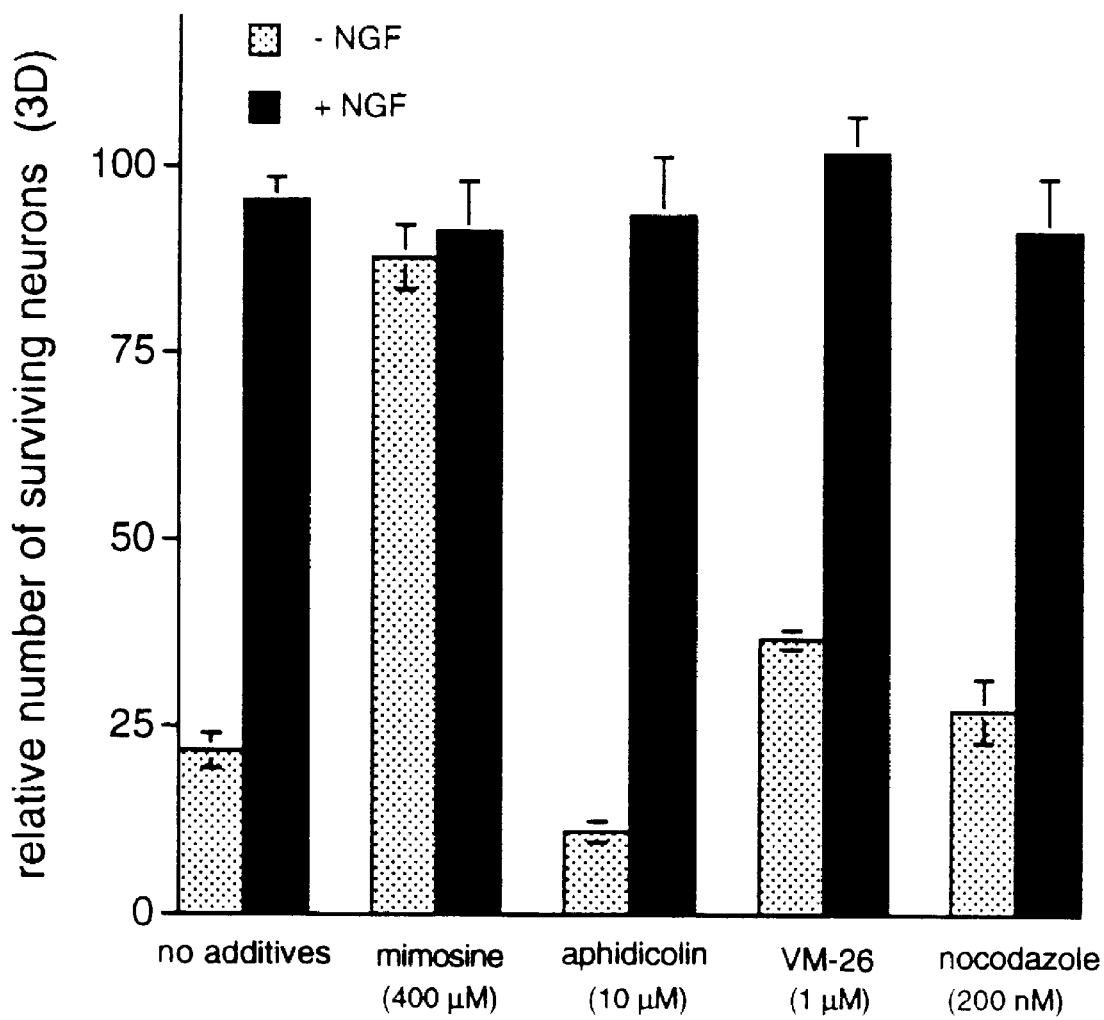
Figure 10A:
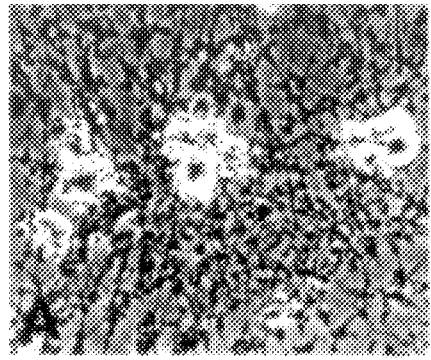
FIGS. 10A, 10B, 10C, 10D, 10E, and 10F show phase contrast micrographs of cultured primary sympathetic neurons maintained for three days after withdrawal of NGF and addition of: (A) no additives; (B) 100 ng/ml NGF; (C) 400 $\mu$M mimosine; (D) 1 mM deferoxamine; (E) no additives (control for CPX experiment); (F) 2 $\mu$M ciclopirox olamine. Magnification is 375×.
Figure 10B:
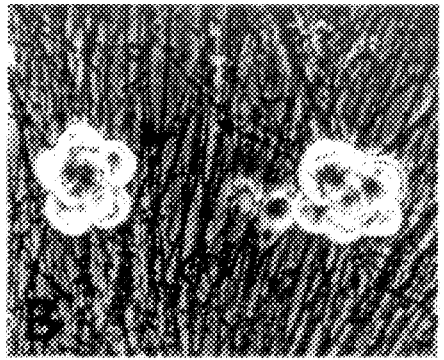
Figure 10C:
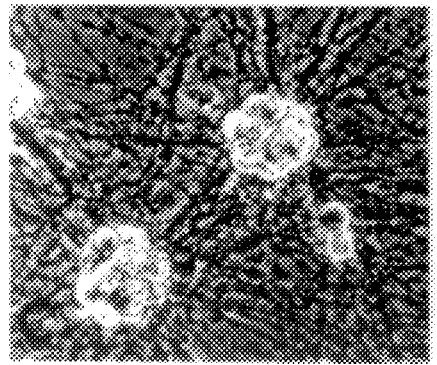
Figure 10D:
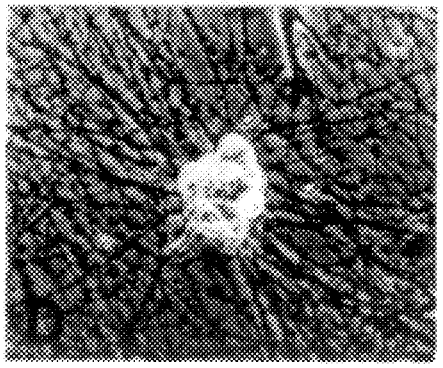
Figure 10E:
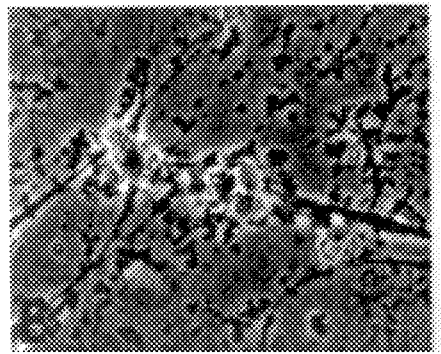
Figure 10F:
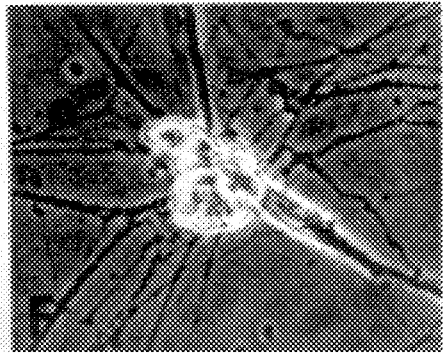

As illustrated in FIG. 9E, treatment of sympathetic neurons with S, G2 and M-phase blockers did not effectively rescue them from death following NGF withdrawal. These blockers were not toxic to the neurons, as viability was maintained when NGF was present in combination.

Discussion

The results demonstrate that mimosine, ciclopirox and deferoxamine inhibit death of trophic-factor-deprived PC12 cells and sympathetic neurons. These findings thus identify several small compounds that interfere with induced neuronal death and provide potential insight into the mechanisms by which trophic agents regulate neuronal survival and apoptosis.

The capacity of G1/S blockers to maintain survival was confirmed by several different criteria. For PC12 cells, quantification of intact nuclei, which has proved a highly reliable indicator of survival in past studies (Batistatou and Greene, 1991; Rukenstein et al., 1991), was supplemented by demonstrating intact metabolic function with Alamar Blue, by showing that cell replication commenced after drug washout and addition of serum, and by differentially staining intact and pyknotic nuclei with Hoechst 33342. In the case of sympathetic neurons, cell survival was assessed not only by the presence of intact, phase bright somas and maintenance of the neuritic network, but also by the observation that drug washout and NGF readdition led to the reappearance of neurite outgrowth and of somatic hypertrophy. Moreover, the majority of cells scored as viable in the presence of the G1/S inhibitors were still identifiable as such several days after the drugs were removed and replaced with NGF.

One mechanism that might account for the protective effects of mimosine, ciclopirox and deferoxamine is their actions as cell cycle inhibitors. It was hypothesized that trophic factors such as NGF promote survival either by guiding proliferating neuroblasts through the cell cycle, by causing neuroblasts to differentiate and leave the cycle or by causing post-mitotic neurons to remain out of the cycle (Ferrari and Greene, 1994). It was further postulated that neuroblast-like cells die after loss of trophic support because they undergo an aborted attempt to proliferate and that withdrawal of trophic factors from post-mitotic neurons results in apoptotic death due to an inappropriate attempt to re-enter the cell cycle (Batistatou and Greene, 1993; Heintz, 1993; Freeman et al., 1994; Rubin et al., 1993; Ferrari and Greene, 1994). This model predicts that appropriately blocking neuronal cells from entering or re-entering the cell cycle should protect them from death caused by loss of trophic support. In accordance with this, blockade of DNA synthesis by induction of dominant-inhibitory ras in both naive and primed PC12 cells (Ferrari and Greene, 1994) or by treatment of PC12 cells and sympathetic neurons with N-acetylcysteine, promotes long-term survival following trophic factor withdrawal. The present data further support and extend these findings.

One issue addressed here was whether blockade at any stage of the cell cycle is sufficient to prevent death of trophic-factor-deprived neuronal cells. Clearly, the present findings indicate that this is not the case; S-, G2- or M-phase blockers were unable to delay or prevent death. Only G1/S blockers were effective in this regard. This suggests that there is a cell cycle checkpoint downstream of, or at the point where these agents block (i.e., near the G1/S border) which once passed, commits neuronal cells to die in the absence of trophic support. cAMP is also an effective G1 blocker (Boynton and Whitfield, 1984; Kato et al., 1994) and our observed close correspondence between the dose-response curves for inhibition of DNA synthesis and promotion of survival by CPT-cAMP can also be taken to support this notion.

The present studies utilized three complementary neuronal death models—proliferating naive PC12 cells, non-proliferating neuronally-differentiated PC12 cells and post-mitotic sympathetic neurons. Several points emerge from comparison of the three systems which support the above interpretation. First, the dose-response relationships for cell cycle blockade by mimosine, CPX and deferoxamine in naive PC12 cells correlate well with the abilities of these drugs to rescue all three cell types from death. This supports not only a link between cell cycle and neuronal death, but is also consistent with a mechanism in which neuronally-differentiated PC12 cells and sympathetic neurons re-enter the cell cycle after withdrawal of trophic support, but are prevented from fatally progressing by these agents. Second, complete rescue of naive PC12 cells by the G1 blockers requires overnight pretreatment prior to serum deprivation, whereas such pretreatment is not necessary for complete rescue of neuronally-differentiated PC12 cells or sympathetic neurons. This difference is in agreement with the prediction of a critical checkpoint before the G1/S border. Without drug pretreatment, naive PC12 cells are unsynchronized, and at the time of trophic factor withdrawal, portions of the population are in S, G2 or M phase. The present findings indicate that cells allowed to enter these portions of the cycle die when deprived of trophic support. With a pretreatment period with G1/S blockers, on the other hand, the cells have the time to continue progression so that they return to G1 where they are then trapped in a safe position prior to the critical checkpoint. Thus, pretreatment is as observed, necessary for complete rescue of naive cells from serum withdrawal. In this case of sympathetic neurons and neuronally-differentiated PC12 cells, the cells are already essentially synchronized in $G_0$. in the presence of NGF and pretreatment is therefore unnecessary for complete rescue by G1/S blockers.

The above interpretations are further supported by observations regarding apoptosis of mature T lymphocytes induced by T cell receptor (TcR) agonists. Susceptibility to TcR agonists occurs only when T cells are induced to proliferate by growth factors such as IL-2 (Lenardo, 1991). Boehme and Lenardo (1993) reported that IL-2 treated mature T lymphocytes were rescued from TcR-induced apoptosis by the G1 inhibitors mimosine, deferoxamine and dibutyryl cAMP, but not by the S-phase inhibitor aphidicolin.

The mechanisms by which mimosine and deferoxamine block proliferation are unclear, but it appears that their ability to chelate metal ions may be critical. Mimosine is a plant amino acid that chelates copper and iron (Hashiguchi and Takahashi, 1977; Kontohiorghes and Evans, 1985). It reversibly inhibits the metallo-enzyme deoxyhypusyl hydroxylase, thus preventing the formation of hypusine, an essential component of the eukaryotic initiation factor 5A (Hanauske-Abel et al., 1994). There is evidence for a correlation between hypusine formation and cell cycle progression (Park et al., 1993). It has also been reported that mimosine causes a decrease in cyclin A/p34cdc2 kinase activity (Carbonaro-Hall et al., 1993; Feldman and Schonthal, 1994) as well as in the corresponding mRNAs for cyclin A and p34cdc2 (Feldman and Schonthal, 1994). Deferoxamine is a microbial siderophore that has a high affinity for iron. Proliferating cells have an essential requirement for iron and iron chelators such as deferoxamine block DNA synthesis (Robbins and Pederson, 1970; Ganeshaguru et al., 1980) and halt the cell cycle prior to the G1/S boundary (Terada et al., 1991). Deferoxamine also prevents the synthesis of p34cdc2 in both lymphocytes and neuroblastoma cells (Terada et al., 1993; Brodie et al., 1993). The mechanism by which ciclopirox blocks cell cycle progression is not known (Hoffman et al., 1991). This agent is used clinically as a topical antifungal and its action in this regard it may involve disruption of membrane function in sensitive organisms (Jue et al., 1985). Owing to its structural similarity with mimosine, the possibility that CPX might chelate metal ions and/or inhibit hypusine formation cannot be excluded, although no such evidence has been reported (Hoffman et al., 1991; Hanauske-Abel et al., 1994).

Because mimosine and deferoxamine are metal chelators, it is prudent to consider the possibility that they may promote survival by inhibiting the formation of reactive oxygen species (ROS). There is reason to consider possible links between oxidative stress and neuronal apoptosis caused by trophic factor withdrawal. Greenlund et al. (1995) reported that there is a transient increase in ROS in sympathetic neurons within hours of NGF withdrawal. Moreover, the latter found that microinjection of copper/zinc superoxide dismutase (SOD) protein or expression vector delayed death of neurons deprived of NGF while injection of antisense SOD accelerated neuronal death. Because readdition of NGF was able to rescue NGF-deprived sympathetic neurons at a point after which injection of SOD cannot, it was suggested that generation of ROS may act to signal downstream events in neuronal programmed cell death (Greenlund et al., 1995). In additional studies, it was observed that trophic agents can protect neurons from conditions that result in oxidative stress and that such agents enhance metabolic pathways by which neurons cope with oxidative stress (Pan and Perez-Polo, 1993; Boniece and Wagner, 1993) and that over-expression of bcl-2 is protective from both oxidative stress (Kane et al., 1993) and loss of trophic support (Garcia et al., 1992; Batistatou et al., 1993; Mah et al., 1993). In addition, Ratan et al., (1994a,b) showed that inhibitors of protein and RNA synthesis protect neurons from apoptosis caused either by withdrawal of growth factors or by induction of oxidative stress by shunting intracellular use of cysteine from protein synthesis to that of glutathione, a major component in cellular protection from oxidative stress. Taken together, these considerations raise the possibility that ROS play a role in the mechanism by which trophic factor deprivation leads to neuronal apoptosis. Moreover, it is even conceivable that ROS might play a role in signaling reentry into the cell cycle.

Despite these considerations, there are several observations that tend to disfavor the likelihood that mimosine and deferoxamine protect neurons from growth factor withdrawal by suppressing oxidative stress. First, antioxidants such as vitamin E, BHA and vitamin C, which prevent death induced by oxidative stress in a variety of cell systems (Sies, 1993; Greenspan and Aruoma, 1994), fail to rescue PC12 cells from trophic factor withdrawal. Particularly germane is the finding that SOD1 depletion in PC12 cells leads to their rapid apoptotic death, presumably via an oxidative stress mechanism (Troy and Shelanski, 1994). In this case, low concentrations of vitamin E effectively prevent death, while long-term NGF exposure does not. Furthermore, although mimosine and deferoxamine prevent death of PC12 cells in the SOD1 depletion model, they do so at concentrations that are orders of magnitude lower than required to block apoptosis and DNA synthesis in the presently studied trophic factor withdrawal paradigm (Troy et al., 1995). These considerations therefore presently indicate that PC12 cell death caused by oxidative stress and by trophic factor removal proceed, at least initially, by separate pathways. The necessary role for oxidative stress in programmed cell death is further questioned by the finding that in certain model systems, including one involving trophic factor deprivation, generation of ROS does not appear to be required for apoptotic death (Jacobson and Raff, 1995).

In summary, the results show that mimosine, deferoxamine, ciclopirox and a permeant cAMP analogue each shows good correlation between the concentrations necessary to block DNA synthesis and to suppress apoptotic death of neuronal cells caused by withdrawal of trophic support. This supports the hypothesis that neuronal cells die when deprived of trophic factors because they attempt abortive cell cycle progression and draws particular attention to a critical checkpoint at or before the G1/S border. Although apparently less likely, an alternative is that these agents protect trophic-factor-deprived cells from death by virtue of their capacities to chelate iron and thereby prevent formation of ROS.

REFERENCES

Adams, R. L. P. and J. G. Lindsay. 1967. Hydroxyurea. Reversal of inhibition and use as a cell-synchronizing agent. *J. Biol. Chem.* 242:1314–1317.

Batistatou, A. and L. A. Greene. 1991. Aurintricarboxylic acid rescues PC12 cells and sympathetic neurons from cell death caused by nerve growth factor deprivation: correlation with suppression of endonuclease activity. *J. Cell Biol.* 115:461–471.

Batistatou, A. and L. A. Greene. 1993. Internucleosomal DNA cleavage and neuronal cell survival/death. *J. Cell Biol.* 122:523–532.

Batistatou, A., D. E. Merry, S. J. Korsmeyer, and L. A. Greene. 1993. Bcl-2 affects survival but not neuronal differentiation of PC12 cells. *J. Neurosci.* 13:4433–4428.

Boehme, S. A. and M. J. Lenardo. 1993. Propriocidal apoptosis of mature T lymphocytes occurs at S phase of the cell cycle. *Eur. J. Immunol.* 23:1552–1560.

Boniece, I. R. and J. A. Wagner. 1993. Growth factors protect PC12 cells against ischemia by a mechanism that is independent of PKA, PKC and protein synthesis. *J. Neurosci.* 13:4220–4228.

Boynton, A. L. and J. F. Whitfield. 1983. The role of cyclic AMP in cell proliferation: a critical assessment of the evidence. *Adv. Cycl. Nucl. Res.* 15:193–294.

Brodie, C., G. Siriwardana, J. Lucas, R. Schleicher, N. Terada, A. Szepesi, E. Gelfand, and P. Seligman. 1993. Neuroblastoma sensitivity to growth inhibition to deferrioxamine: evidence for a block in Gi phase of the cell cycle. *Cancer Res.* 53:3968–3975.

Carbonaro-Hall, D., R. Williams, L. Wu, D. Warburton, M. Zeichner-David, V. Tolo, and F. Hall. 1993. G1 expression and multistage dynamics of cyclin A in human osteosarcoma cells. *Oncogene* 8:1649–1659.

Chen, M. and W. T. Beck. 1993. Teniposide-resistant CEM cells, which express mutant DNA topoisomerase IIa, when treated with non-complex-stabilizing inhibitors of the enzyme, display no cross-resistance and reveal functions of the mutant enzyme. *Cancer Res.* 53:5946–5953.

Colombel, M., C. A. Olsson, P. Y. Ng, and R. Buttyan. 1992. Hormone-regulated apoptosis results from reentry of differentiated prostate cells onto a defective cell cycle. *Cancer Res.* 52:4313–4319.

Deckwerth, T. L. and E. M. Johnson, Jr. 1993. Temporal analysis of events associated with programmed cell death (apoptosis) of sympathetic neurons deprived of nerve growth factor. *J. Cell Biol.* 123:1207–1222.

Edwards, S. N., A. E. Buckmaster, and A. M. Tolkovsky. 1991. The death programme in cultured sympathetic neurones can be suppressed at the post-translational level by nerve growth factor, cyclic AMP and depolarization. *J. Neurochemistry* 57:2140–2143.

Edwards, S. N. and A. M. Tolkovsky. 1994. Characterization of apoptosis in cultured rat sympathetic neurons after nerve growth factor withdrawal. *J. Cell Biol.* 124:537–546.

Evan, G. E., A. H. Wyllie, C. S. Gilbert, T. D. Littlewood, H. Land, M. Brooks, C. M. Waters, L. Z. Penn, and D. C. Hancock. 1992. Induction of apoptosis in fibroblasts by c-myc protein. *Cell* 69:119–128.

Feldman, S. T. and A. Schonthal. 1994. Negative regulation of histone Hi kinase expression by mimosine, a plant amino acid. *Cancer Res.* 54:494–498.

Ferrari, G. and L. A. Greene. 1994. Proliferative inhibition by dominant-negative Ras rescues naive and neuronally-differentiated PC12 cells from apoptotic death. *EMBO J.* 13:5922–5928.

Freeman, R. F., S. Estus, and E. M. Johnson, Jr. 1994. Analysis of cell-related gene expression in postmitotic neurons: selective induction of Cyclin D1 during programmed cell death. *Neuron* 12:343–355.

Ganeshaguru, K., A. V. Hoffbrand, R. W. Grady, and A. Cerami. 1980. Effects of various iron chelating agents on DNA synthesis in human cells. *Biochem. Pharm.* 29:1275–1279.

Garcia, I., I. Martinou, Y. Tsujimoto, and J. C. Martinou. 1992. Prevention of programmed cell death of sympathetic neurons by the bcl-2 proto-oncogene. *Science* 258:302–304.

Greene, L. A. 1978. Nerve growth factor prevents the death and stimulates neuronal differentiation of clonal PC12 pheochromocytoma cells in serum-free medium. *J. Cell Biol.* 78:747–755.

Greene, L. A., M. M. Sobeih, and K. K. Teng. 1991. Methodologies for the culture and experimental use of the PC12 rat pheochromocytoma cell line. In Culturing Nerve Cells. G. Banker and K. Goslin, editors. MIT Press, Cambridge. 207–226.

Greene, L. A. and A. S. Tischler. 1976. Establishment of a noradrenergic clonal line of rat adrenal pheochromocytoma cells which respond to nerve growth factor. *Proc. Natl. Acad. Sci.* 73:2424–2428.

Greene, L. A. and A. S. Tischler. 1982. PC12 pheochromocytoma cells in neurobiological research. *Adv. Cell. Neurobiol.* 3:373–414.

Greenlund, L. J. S., Deckwerth, T. L. and E. M. Johnson, Jr. 1995. Superoxide dismutase delays neuronal apoptosis: a role for reactive oxygen species in programmed neuronal death. *Neuron.* 14:303–315.

Greenspan, H. C. and O. I. Aruoma. 1994. Oxidative stress and apoptosis in HIV infection: a role for plant-derived metabolites with synergistic antioxidant activity. *Immunol. Today* 15:209–213.

Guroff, G. 1985. PC12 cells as a model of neuronal differentiation. In Cell Culture in Neuroscience. J. E. Bottenstein and G. Sato, editors. Plenum, New York. 245–266.

Hanauske-Abel, H. M., M. H. Park, A. R. Hanauske, A. M. Popowicz, M. Lalande, and J. E. Polk. 1994. Inhibition of the G1-S transition of the cell cycle by inhibitors of deoxyhypusine hydroxylation. *Biochim. Biophys. Acta* 1221:115–124.

Hashiguchi, H. and H. Takahashi. 1977. Inhibition of two copper-containing enzymes, tyrosine and dopamine b-hydroxylase, by L-mimosine. *Molec. Pharm.* 13:362–367.

Heintz, N. 1993. Cell death and the cell cycle: a relationship between transformation and neurodegeneration? *Trends in Biochemical Sciences* 18:157–159.

Hoffman. B. D., H. M. Hanauske-Abel, A. Flint and M. Lalande. 1991. A new class of reversible cell cycle inhibitors. *Cytometry* 12:26–32.

Ikegami, S., T. Taguchi, M. Ohashi, M. Oguro, H. Nagano, and Y. Mano. 1978. Aphidicolin prevents mitotic division by interfering with the activity of DNA polymerase-a. *Nature* 275:458–460.

Jackson, R. C. 1978. The regulation of thymidylate biosynthesis in Novikoff hepatoma cells and the effects of amethopterin, 5-fluorodeoxyuridine, and 3-deazauridine. *J. Biol. Chem.* 253:7440–7446.

Jacobson, M. D. and M. C. Raff. 1995. Programmed cell death and Bcl-2 protection in very low oxygen. *Nature* 374:814–816.

Jue, S. G., Dawson, G. W. and R. N. Brogden. 1985. Ciclopirox olamine 1% cream. A preliminary review of its antimicrobial activity and therapeutic use. *Drugs.* 29:330–341.

Kane, D. J., T. A. Sarafian, R. Anton, H. Hahn, E. B. Gralla, J. S. Valentine, T. Ord, and D. E. Bredesen. 1993. Bcl-2 inhibition of neural death: decreased generation of reactive oxygen species. *Science* 262:1274–1277.

Kato, J., M. Matsuoka, K. Polyak, J. Massague, and C. J. Sherr. 1994. Cyclic AMP-induced G1 phase arrest mediated by an inhibitor ($p_{27}^{KiP1}$) of cyclin-dependent kinase 4 activation. *Cell* 79:487–496.

Kontoghiorges, G. J. and R. W. Evans. 1985. Site specificity of iron removal from transferrin by a-ketohydroxypyridine chelators. *FEBS Letters* 189:141–144.

Lalande, M. 1990. A reversible arrest point in the late G1 phase of the mammalian cell cycle. *Exp. Cell Res.* 186:332–339.

Lee, V. M., M. L. Shelanski, and L. A. Greene. 1980. Characterization of antisera raised against cultured rat sympathetic neurons. *Neuroscience* 5:2239–2245.

Lenardo, M. J. 1991. Interleukin-2 programs mouse ab T lymphocytes for apoptosis. *Nature* 353:858–861.

Mah, S. P., L. T. Zhong, Y. Liu, A. Roghani, R. H. Edwards, and D. E. Bredesen. 1993. The protooncogene bcl-2 inhibits apoptosis in PC12 cells. *J. Neurochem.* 60:1183–1186.

Martin, D. P., A. I. Ito, K. Horigome, P. A. Lampe, and E. M. Johnson, Jr. 1992. Biochemical characterization of programmed cell death in NGF-deprived sympathetic neurons. *J. Neurobiol.* 23:1205–1220.

Martin, D. P., R. E. Schmidt, P. S. DiStefano, O. H. Lowry, J. G. Carter, and E. M. Johnson, Jr. 1988. Inhibitors of protein synthesis and RNA synthesis prevent neuronal death caused by nerve growth factor deprivation. *J. Cell Biol.* 106:829–844.

Mesner, P. W., T. R. Winters, and S. H. Green. 1992. Nerve growth factor-withdrawal induced cell death in neuronal PC12 cells resembles that in sympathetic neurons. *J. Cell Biol.* 119:1669–1680.

Pan, Z. and R. Perez-Polo. 1993. Role of nerve growth factor in oxidant homeostasis: glutathione metabolism. *J. Neurochem.* 61:1713–1721.

Park, M. H., E. C. Wolff, and J. E. Folk. 1993. Is hypusine essential for eukaryotic cell proliferation? *Trends Biochem. Sci.* 18:475–479.

Pittman, R. N., S. Wang, A. J. Di Benedetto, and J. Mills. 1993. A system for characterizing cellular and molecular events in programmed neuronal cell death. *J. Neurosci.* 13:3669–3680.

Poon, R. Y. C., K. Yamashita, J. P. Adamczewski, T. Hunt, and J. Shuttleworth. 1993. The cdc2-related protein p40$^{MO15}$ is the catalytic subunit of a protein kinase that can activate p33$^{cdk2}$ and p34$^{cdc2}$ *EMBO J.* 12:3123–3132.

Ratan, R. R., T. H. Murphy, and J. M. Baraban. 1994. Macromolecular synthesis inhibitors prevent oxidative stress-induced apoptosis in embryonic cortical neurons by shunting cysteine from protein synthesis to glutathione. *J. Neurosci.* 14:4385–4392.

Ratan, R. R., T. H. Murphy, and J. M. Baraban. 1994. Oxidative stress induces apoptosis in embryonic cortical neurons. *J. Neurochem.* 62:376–379.

Robbins, E. and T. Pederson. 1970. Iron: its intracellular localization and possible role in cell division. *Proc. Natl. Acad. Sci.* 66:1244–1251.

Roberge, M., J. Th'ng, J. Hamaguchi, and E. M. Bradbury. 1990. The topoisomerase inhibitor VM-26 induces marked changes in histone H1 kinase activity, histones H1 and H3 phosphorylation, and chromosome condensation in G2 phase and mitotic BHK cells. *J. Cell Biol.* 111:1753–1762.

Rubin, L. L., K. L. Philpott, and S. F. Brooks. 1993. The cell cycle and cell death. *Curr Biology* 3:391–394.

Rudkin, B. B., P. Lazarovici, B. Levi, Y. Abe, K. Fujita, and G. Guroff. 1989. Cell cycle-specific action of nerve growth factor in PC12 cells: differentiation without proliferation. *EMBO J.* 8:3319–3325.

Rukenstein, A., R. E. Rydel, and L. A. Greene. 1991. Multiple agents rescue PC12 cells from serum-free cell death by translation- and transcription-independent mechanisms. *J. Neurosci.* 11:2552–2563.

Rydel, R. E. and L. A. Greene. 1988. cAMP analogs promote survival and neurite outgrowth in cultures of rat sympathetic and sensory neurons independently of nerve growth factor. *Proc. Natl. Acad. Sci.* 85:1257–1261.

Schiff, P. B., J. Fant, and S. B. Horwitz. 1979. Promotion of microtubule assembly in vitro by taxol. *Nature* 277:665–667.

Shi, L., W. K. Nishioka, J. Th'ng, E. M. Bradbury, D. W. Litchfield, and A. H. Greenberg. 1994. Premature p34$^{cdc2}$ activation required for apoptosis. *Science* 263:1143–1145.

Sies, H. 1993. Strategies of antioxidant defense. *Eur. J. Biochem.* 215:213–219.

Soto, A. M. and C. Sonnenschein. 1985. The role of estrogens on the proliferation of human breast tumor cells (MCF-7). *J. Steroid. Biochem.* 23:87–94.

Terada, N., J. J. Lucas, and E. W. Gelfand. 1991. Differential regulation of the tumor suppressor molecules, retinoblastoma susceptibility gene product (Rb) and p53, during cell cycle progression of normal human T cells. *J. Immunol.* 147:698–704.

Terada, N., R. Or, A. Szepesi, J. J. Lucas, and E. W. Gelfand. 1993. Definition of the roles for iron and essential fatty acids in cell cycle progression of normal human T lymphocytes. *Exp. Cell Res.* 204:260–267.

Tischler, A. S., J. C. Riseberg, M. A. Hardenbrook, and V. Cherington. 1993. Nerve growth factor is a potent inducer of proliferation and neuronal differentiation for adult rat chromaffin cells in vitro. *J. Neurosci.* 13:1533–1542.

Troy, C. M., D. Derossi, A. Prochiantz, L. A. Greene and M. L. Shelanski. Down-regulation of SOD1 leads to cell death by the NO-peroxynitrite pathway. *J. Neurosci. (in press)*.

Troy, C. M. and M. L. Shelanski. 1994. Down-regulation of copper/zinc superoxide dismutase causes apoptotic death in PC12 neuronal cells. *Proc. Natl. Acad. Sci.* 91:6384–6387.

Wilson, L. and M. A. Jordan. 1994. Pharmacological probes of microtubule function. In Microtubules. J. S Hyams, and C. W. Lloyd, editors. Wiley-Liss, Inc., New York. 59–83.

Yonish-Rouach, E., D. Grunwald, S. Wilder, A. Kimchi, E. May, J. J. Lawrence, P. May, and M. Oren. 1993. P53-mediated cell death: relationship to cell cycle control. *Mol. Cell Biol.* 13:1415–1423.

Yonish-Rouach, E., D. Resnitzky, J. Lotem, L. Sachs, A. Kimchi, and M. Oren. 1991. Wild-type p53 apoptosis of myeloid leukaemic cells that is inhibited by interleukin-6. *Nature* 352:345–347.

What is claimed is:

1. A method of treating neuronal cell damage or neuronal cell death in a subject who is known to have neuronal cell-damage or neuronal cell death comprising administering to the subject 6-cyclohexyl-1-hydroxy-4-methyl-2(1H)-pyridinone or a pharmaceutically acceptable salt thereof, the 6-cyclohexyl-1-hydroxy-4-methyl-2(1H)-pyridinone or salt thereof being administered in an amount effective to inhibit neuronal cell damage or neuronal cell death in the subject.

2. The method of claim 1, wherein the subject is a mammal.

3. The method of claim 2, wherein the mammal is a human.

4. The method of claim 2, wherein the mammal is a mouse.

5. The method of claim 1, wherein the neuronal cell damage or neuronal cell death is associated with a traumatic injury.

6. The method of claim 1, wherein the neuronal cell damage or neuronal cell death is associated with a stroke.

7. The method of claim 1, wherein the neuronal cell damage or neuronal cell death is associated with a disease selected from the group consisting of Parkinson's disease, amyotrophic lateral sclerosis, and Alzheimer's disease.

8. The method of claim 1, wherein the effective amount of 6-cyclohexyl-1-hydroxy-4-methyl-2(1H)-pyridinone or salt thereof is from about 5 mg/Kg of body weight to about 30 mg/Kg of body weight per day.

9. The method of claim 8, wherein the effective amount of 6-cyclohexyl-1-hydroxy-4-methyl-2(1H)-pyridinone or salt thereof is from about 10 mg/Kg of body weight to about 20 mg/Kg of body weight per day.

10. The method of claim 1, wherein the salt is the ethanolamine salt of 6-cyclohexyl-1-hydroxy-4-methyl-2 (1H)-pyridinone.

11. The method of claim 1, wherein the 6-cyclohexyl-1-hydroxy-4-methyl-2(1H)-pyridinone or salt thereof is administered orally, intravenously, subcutaneously, intramuscularly, topically, parenterally, by inhalation, rectally, or intraocularly.

12. A method of treating neuronal cell damage or neuronal cell death in a subject comprising inhibiting neuronal cell damage or neuronal cell death according to claim 1.

\* \* \* \* \*